United States Patent [19]
Sato et al.

[11] Patent Number: 5,721,213
[45] Date of Patent: Feb. 24, 1998

[54] PEPTIDES, ACTIVE AS INHIBITORS OF PLATELET AGGREGATION

[75] Inventors: Yoshimi Sato; Yoshio Hayashi; Jun Katada, all of Kawasaki, Japan

[73] Assignee: Nippon Steel Corporation, Kawasaki, Japan

[21] Appl. No.: 596,116

[22] PCT Filed: Sep. 29, 1994

[86] PCT No.: PCT/JP94/01611

§ 371 Date: Jan. 30, 1996

§ 102(e) Date: Jan. 30, 1996

[87] PCT Pub. No.: WO95/09185

PCT Pub. Date: Apr. 6, 1995

[30] Foreign Application Priority Data

Sep. 30, 1993 [JP] Japan ................................. 5-245541
Mar. 22, 1994 [JP] Japan ................................. 6-050602

[51] Int. Cl.$^6$ ........................... A61K 38/08; C07K 7/06
[52] U.S. Cl. ........................................ 514/17; 530/329
[58] Field of Search ............................ 514/17; 530/329

[56] References Cited

U.S. PATENT DOCUMENTS 5,498,601   3/1996   Sato et al. ............................ 514/17

Primary Examiner—Jeffrey E. Russel
Attorney, Agent, or Firm—Kenyon & Kenyon

[57] ABSTRACT

The present invention provides compounds and salts thereof, that are represented by the formula:

Pro-Ser-A-B-Asp-C-D wherein A is an amino acid which does not contain a guanidino group as a side chain, B is a amino acid, C is a hydrophobic amino acid and D is a hydroxy group or an amino acid. The compounds of the invention have excellent platelet aggregation inhibiting and blood coagulation inhibiting activities. Also provided are reagents, pharmaceutical compositions and methods for inhibiting platelet aggregation and blood coagulation.

27 Claims, 4 Drawing Sheets

Blood Coagulation-inhibiting Effect in a Dog Hemodialysis Model

Protective effect against the decrease in platelet count during storage

PEPTIDES, ACTIVE AS INHIBITORS OF PLATELET AGGREGATION

TECHNICAL FIELD

The present invention relates to novel peptides having platelet aggregation-inhibiting action, and platelet aggregation-inhibiting agents, blood coagulation-inhibiting agents for extracorporeal circulation, cell adhesion-inhibiting agents, tumor metastasis-inhibiting agents and agents for protecting platelet preparations for blood transfusion which comprise the novel peptides as an active ingredient, as well as platelet preparations for blood transfusion in which the novel peptides are added and platelet preparation packs for blood transfusion which comprise the novel peptides in the platelet preparations for blood transfusion in the packs.

BACKGROUND ART

Platelets play an important role in hemostasis by adhering to the surface of a damaged blood vessel.

However, it is known that platelet aggregation is primarily responsible for the formation of thrombus and that the formed thrombus obstructs a blood vessel. This obstruction prevents the adequate supply of oxygen and nutrients to tissues and organs and thereby causes ischemic diseases in circulatory organs as represented by myocardial infarction and cerebral infarction. At present, the mortality rates of these ischemic diseases follow that of cancer, which has become a significant social problem.

When medical treatments involving the extracorporeal circulation of blood, as exemplified by the use of an artificial heart and lung during surgical operations and renal dialysis for patients with renal failure, are conducted, blood coagulation may be caused by the activation and aggregation of platelets, which adversely affects the performance of such medical treatments.

Thus, the prevention of thrombus formation and blood coagulation is an important matter in avoiding the occurrence of ischemic diseases or in safely conducting extracorporeal circulation.

Platelets are activated by the binding, to receptors on a platelet membrane, of thrombin present in plasma, connective tissue proteins such as collagen present in subendothelial tissues that may become exposed by damage to a blood vessel and other substances. Platelets are also activated by the binding of released adenosine diphosphate (ADP), adrenaline, serotonin, thromboxane (TX) A2 and the like to membrane receptors in a manner like autosecretion. Two kinds of glycoprotein units which compose a fibrinogen receptor are presented on the cell surface and associated to form a receptor complex (gpIIbIIIa), whereby aggregation via a fibrinogen bridge is induced.

Patients with thrombasthenia characterized by congenital absence of gpIIb and gpIIIa do not have a capability for platelet aggregation. Therefore, it is clear that the binding of the gpIIbIIIa complex to fibrinogen is essential to platelet aggregation (Rouslahti et al., Science, 238, 491 (1987)).

Attempts have been made to prevent thrombus formation by the inhibition of platelet aggregation utilizing the properties of the gpIIbIIIa complex.

For example, Coller et al. reported that an F(ab')$_2$ fragment of a monoclonal antibody against the gpIIbIIIa complex has a strong inhibitory action on platelet aggregation and verified that a platelet aggregation-inhibiting agent could be developed utilizing this action (Blood, 68, 783, (1986)).

Although it is recognized that the monoclonal antibody has the potential as a therapeutic agent for inhibiting platelet aggregation, there is apprehension concerning the possible production of antibodies against the monoclonal antibody by its repeated administration, since it is in itself a large protein.

Therefore, it has been desired to develop platelet aggregation-inhibiting agents containing as active ingredients non-immunogenic small compounds that have the properties of antagonists to the gpIIbIIIa complex.

Studies on the binding of fibrinogen to the gpIIbIIIa complex have been conducted aggressively. These studies started with the finding of arginine-glycine-aspartic acid (RGD) as an amino acid sequence common to cell adhesive molecules by a series of studies conducted by Ruoslahti et al. (Ruoslahti et al., Nature 309, 30–33 (1984)). The study of receptors recognizing the RGD sequence verified that the gpIIbIIIa complex is a receptor classified in an integrin family recognizing the RGD sequence (Phillips et al., Blood, 71, 831–843 (1988)) and that this complex especially recognizes two arginine-glycine-aspartic acid-phenylalanine (RGDF) (SEQ ID NO:68) sequences present in the fibrinogen molecule, thereby binding with the fibrinogen (Andrieux et al., J. Biol. Chem., 264, 9258–9265 (1989)).

Furthermore, it is known that the gpIIbIIIa complex binds to von Willebrand factor, fibronectin, vitronectin and thrombospondin which have the RGD sequence as well as fibrinogen (Pytela et al., Science., 231, 1559 (1986) and Cell, 42, 439 (1985)).

It is expected from these findings that synthetic peptides containing the RGD sequence inhibit the binding of the gpIIbIIIa complex to fibrinogen and thereby inhibit platelet aggregation. In fact, it was reported that 400µM of a synthetic peptide glycine-arginine-glycine-aspartic acid-serine-proline (GRGDSP) (SEQ ID NO:69) completely inhibited the aggregation of platelets activated by ADP (Plow et al., Proc. Natl. Acad. Sci. USA., 82, 8057–8061 (1985)). In addition, it has been verified that arginine-glycine-aspartic acid-serine (RGDS) (SEQ ID NO:70) at concentrations of 46–50µM inhibits 80–90% of platelet aggregation in a concentration-dependent manner (Plow et al., Blood, 70, 110–115 (1987)). Moreover, it has been revealed that a peptide RGDF (SEQ ID NO:68)exhibits platelet aggregation-inhibiting activity 4–5 times as strong as RGDS (SEQ ID NO:70) (Harfinest et al., 71, 132–136 (1988)).

Japanese unexamined patent publication (hereinafter referred to as "KOKAI") Nos. Hei 1-190699 and Hei 2-62892, EPO 422937 A1 and U.S. Pat. (hereinafter referred to as "USP") No. 4,952,562 disclose tetrapeptide derivatives containing the RGD sequence. KOKAI No. Sho 63-215696 discloses other peptide derivatives containing the RGD sequence. KOKAINs. Hei 3-118331 and Hei 2-62892 and WO 91/01331 disclose derivatives having the cyclic structure of the RGD peptide.

In recent years, in order to develop agents having high platelet aggregation-inhibiting action and excellent in vivo stability, there have been aggressively conducted studies in which compounds having a structure which does not naturally occur are derived from RGD peptide as a key compound (Hartman et al., J. Med. Chem., 35, 4640–4642 (1992) and Callahan et al., ibid, 35, 3970–3972 (1992)). These compounds are useful as platelet aggregation-inhibiting agents for oral administration which are susceptible to the action of protease.

However, they are expected to manifest toxicity (this problem often occurs in the derivation to non-natural structures) and to have such a side effect that the drugs are not metabolized but accumulated in the human body. Hence, there exists a strong concern for safety.

An improvement in the in vivo stability of compounds leads to the persistence of platelet aggregation-inhibiting action and blood coagulation-inhibiting action, thereby potentially inhibiting for a long period of time the important physiological actions inherently possessed by platelets, as exemplified by the inducement of hemorrhagic tendency and the like.

It has been reported that at the time of extracorporeal circulation, even heparin from an organism which is actually administered to suppress blood coagulation has such a significant side effect that it acts beyond an appropriate period and thereby hemorrhagic tendency is induced (Tadao Akizawa, et al., NIHON RINSHO, vol. 43, 377–391 (1985)).

As described in "Background Art", the RGD peptides per se do not have such high platelet aggregation-inhibiting action as to warrant use in clinical practice. However, the RGD peptides have an excellent characteristic in that they are broken down by protease inherently present in an organism to amino acids which are safe and useful to the organism.

The inventors intended to utilize this characteristic in producing peptide derivatives having excellent platelet aggregation-inhibiting and blood coagulation-inhibiting abilities, platelet-protecting action and cell adhesion-inhibiting activity and to use these compounds as pharmaceutical agents.

An object of the present invention is to provide highly safe peptides and salts thereof having excellent platelet aggregation-inhibiting and blood coagulation-inhibiting abilities, platelet-protecting action and cell adhesion-inhibiting activity.

Another object of the present invention is to provide platelet aggregation-inhibiting agents, blood coagulation-inhibiting agents for extracorporeal circulation, cell adhesion-inhibiting agents, tumor metastasis-inhibiting agents and agents for protecting platelet preparations for blood transfusion which comprise the peptides or salts thereof as an active ingredient, as well as platelet preparations for blood transfusion in which the peptides or salts thereof are added and platelet preparation packs for blood transfusion which comprise the peptides or salts thereof in the platelet preparations for blood transfusion in the packs.

A further object of the present invention is to provide pharmaceutical compositions comprising the peptides or salts thereof as an active ingredient, especially for inhibiting platelet aggregation, blood coagulation at the time of extracorporeal circulation, cell adhesion and tumor metastasis and for protecting platelets in platelet preparations for blood transfusion.

Still further objects of the present invention are to provide methods for inhibiting platelet aggregation, methods for inhibiting blood coagulation at the time of extracorporeal circulation, methods for inhibiting cell adhesion, methods for inhibiting tumor metastasis, and methods for protecting platelets in platelet preparations for blood transfusion by utilizing the peptides or salts thereof.

DISCLOSURE OF INVENTION

As a result of the various studies conducted to solve the above problems, the inventors produced highly active and safe peptide compounds that have excellent platelet aggregation-inhibiting and blood coagulation-inhibiting activities and which are of practical use. Surprisingly, the peptides of the present invention have these activities at very high levels although they do not contain the RGD sequence which is believed to be essential for the platelet aggregation-inhibiting action.

The subject matters of the present invention are as follows:

(1) compounds or salts thereof, that are represented by the following general formula (I):

Pro-Ser-A-B-Asp-C-D (SEQ ID NO:71)   (I)

wherein A is an amino acid other than amino acids having a guanidino group at a side chain, B is an amino acid, C is an amino acid having a hydrophobic group at a side chain and D is a hydroxy or an amino group;

(2) platelet aggregation-inhibiting agents comprising the compounds or salts thereof according to (1) as an active ingredient;

(3) blood coagulation-inhibiting agents for extracorporeal circulation, comprising the compounds or salts thereof according to (1) as an active ingredient;

(4) cell adhesion-inhibiting agents comprising the compounds or salts thereof according to (1) as an active ingredient;

(5) tumor metastasis-inhibiting agents comprising the compounds or salts thereof according to (1) as an active ingredient;

(6) agents for protecting platelet preparations for blood transfusion, comprising the compounds or salts thereof according to (1) as an active ingredient;

(7) platelet preparations for blood transfusion, in which compounds or salts thereof according to (1) are added;

(8) platelet preparation packs for blood transfusion, comprising the compounds or salts thereof according to (1) in platelet preparations for blood transfusion in the packs;

(9) pharmaceutical compositions comprising the compounds or salts thereof according to (1) and a pharmaceutically acceptable carrier;

(10) methods for inhibiting platelet aggregation, comprising the step of administering to a patient an effective amount of the compounds or salts thereof according to (1) in a pharmaceutically acceptable carrier;

(11) methods for inhibiting the coagulation of blood for extracorporeal circulation, comprising the step of administering to a patient an effective amount of the compounds or salts thereof according to (1) in a pharmaceutically acceptable carrier;

(12) methods for inhibiting cell adhesion, comprising the step of administering to a patient an effective amount of the compounds or salts thereof according to (1) in a pharmaceutically acceptable carrier;

(13) methods for inhibiting tumor metastasis, comprising the step of administering to a patient an effective amount of the compounds or salts thereof according to (1) in a pharmaceutically acceptable carrier; and

(14) methods for protecting platelets in platelet preparations for blood transfusion, comprising the step of adding an effective amount of the compounds or salts thereof according to (1) to the platelet preparations.

BEST MODE FOR CARRYING OUT THE INVENTION

In the present invention, the term "amino acid" means a molecule having an amino and a carboxyl group in the molecule.

In the above formula (I), the Pro-Ser structure at the N-terminus consists of a combination of proline having a basic portion at the N-terminus with serine having a hydroxy group at a side chain. The Asp-C structure at the C-terminus consists of a combination of aspartic acid which is an acidic amino acid having a carboxyl group at a side chain with an amino acid having a hydrophobic group at a side chain (hereinafter referred to as "hydrophobic amino acid").

In the peptides of the present invention, the presence of proline having a basic portion and aspartic acid having an acidic portion is required for the platelet aggregation-inhibiting and blood coagulation-inhibiting activities. Furthermore, in order to enhance both activities, the presence of both a structure that connects the basic and acidic portions and thereby fixes the steric location thereof and a structure that interacts with the gpIIbIIIa complex through a hydrophobic bond, a hydrogen bond and the like is important.

The imino group present in the proline at the N-terminus corresponds to the basic portion and the carboxyl group present at a side chain in the aspartic acid corresponds to the acidic portion. The serine or amino acids as A and B, and the hydrophobic amino acid as C in the peptide represented by general formula (I) facilitate the formation of a hydrogen bond and a hydrophobic bond that take part in the formation of the above-described important structures for enhancing the platelet aggregation-inhibiting and blood coagulation-inhibiting activities.

In the formula (I), A is an amino acid which does not have a guanidino group at a side chain and includes neutral amino acids, amino acids having at a side chain an amino group which may substituted with an alkyl group having 1–10 carbon atoms and derivatives thereof, such as p-aminocyclohexyl glycine, p-aminocyclohexyl alanine, p-aminophenylglycine, p-aminophenyl alanine and the like.

In the present invention, the term "side chain" means the portion of R in the following general formula of amino acids.

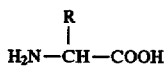

In the present invention, the term "neutral amino acid" means amino acids having a group without electric charges at a side chain, as well as glycine, proline, or derivatives thereof. Examples of the glycine derivatives include N-alkyl glycine having an alkyl group with 1–10 carbon atoms. Examples of the proline derivatives includes proline having a substituted group, an unsaturated bond and a hetero atom in the ring, and proline having different ring sizes. Examples of the group without electric charges at a side chain include substituted or unsubstituted alkyl groups having 1–30 carbon atoms, substituted or unsubstituted aryl groups, substituted or unsubstituted heteroaryl groups, substituted or unsubstituted cycloalkyl groups having 3–10 carbon atoms, and combinations thereof. These groups may further have a group without electric charges which contains a hetero atom such as oxygen, sulfur, or the like. Examples of such a group include hydroxy, mercapto groups, and alkylthio groups having 1–10 carbon atoms.

Specifically, when the side chain is a methyl group, the neutral amino acid is alanine.

When the side chain is an alkyl group, it is preferably a linear or branched type such that the neutral amino acid containing it is relatively highly soluble in water and more preferred examples in terms of its steric hindrance are alkyl groups having 1–20 carbon atoms such as methyl, ethyl, n-propyl, isopropyl, n-butyl, isobutyl, sec-butyl, t-butyl, n-pentyl, n-hexyl, heptyl, and octyl groups.

The preferred examples of the neutral amino acids having an alkyl group at a side chain include alanine, valine, norvaline, leucine, norleucine, tertiary leucine, isoleucine, alloisoleucine and the like. Among them, neutral amino acids having at a side chain an n-propyl or n-butyl group that are linear-type alkyl groups are especially preferred. For example, comparing peptides containing valine or leucine having a bulky isopropyl or isobutyl group (compounds prepared in Examples 3 and 6) with peptides containing norvaline or norleucine having an n-propyl or n-butyl group that are linear-type groups having the same number of carbon atoms (compounds prepared in Examples 5 and 9), the peptides having norvaline or norleucine with a linear alkyl group as a neutral amino acid tend to have higher platelet aggregation-inhibiting and blood coagulation-inhibiting activities.

Preferred examples of the neutral amino acids having a linear alkyl group at a side chain include:
Pro-Ser-Nva-Gly-Asp-Trp-OH (SEQ ID NO:1), Pro-Ser-Nva-Sar-Asp-Trp-OH (SEQ ID NO:2),
Pro-Ser-Nva-Ala-Asp-Trp-OH (SEQ ID NO:3), Pro-Ser-Nle-Gly-Asp-Trp-OH (SEQ ID NO:4),
Pro-Ser-Nle-Sar-Asp-Trp-OH (SEQ ID NO:5), Pro-Ser-Nle-Ala-Asp-Trp-OH (SEQ ID NO:6),
Pro-Ser-Ala-Gly-Asp-Trp-OH (SEQ ID NO:7), Pro-Ser-Ala-Sar-Asp-Trp-OH (SEQ ID NO:8),
Pro-Ser-Ala-Ala-Asp-Trp-OH (SEQ ID NO:9), Pro-Ser-Ala-Sar-Asp-Phe-OH (SEQ ID NO:10),
Pro-Ser-Gly-Gly-Asp-Trp-OH (SEQ ID NO:11), Pro-Ser-Gly-Sar-Asp-Trp-OH (SEQ ID NO:12),
Pro-Ser-Gly-Ala-Asp-Trp-OH (SEQ ID NO:13), Pro-Ser-Met-Gly-Asp-Trp-OH (SEQ ID NO:14),
Pro-Ser-Met-Ala-Sar-Trp-OH (SEQ ID NO:15), Pro-Ser-Met-Ala-Asp-Trp-OH (SEQ ID NO:16),
Pro-Ser-Cys-Gly-Asp-Trp-OH (SEQ ID NO:17), and Pro-Ser-Pen-Gly-Asp-Trp-OH (SEQ ID NO:18).

More preferred examples include:
Pro-Ser-Nva-Gly-Asp-Trp-OH (SEQ ID NO:1)and Pro-Ser-Nle-Gly-Asp-Trp-OH (SEQ ID NO:4).

The most preferred examples include Pro-Ser-Nva-Gly-Asp-Trp-OH (SEQ ID NO:1).

Preferred examples of the neutral amino acids having a branched-type alkyl group at a side chain include:
Pro-Ser-Tle-Gly-Asp-Trp-OH (SEQ ID NO:19), Pro-Ser-Tle-Sar-Asp-Trp-OH (SEQ ID NO:20),
Pro-Ser-Tle-Ala-Asp-Trp-OH (SEQ ID NO:21), Pro-Ser-Tle-Gly-Asp-Phe-OH (SEQ ID NO:22),
Pro-Ser-Tle-Sar-Asp-Phe-OH (SEQ ID NO:23), Pro-Ser-Val-Gly-Asp-Trp-OH (SEQ ID NO:24),
Pro-Ser-Val-Sar-Asp-Trp-OH (SEQ ID NO:25), Pro-Ser-Val-Ala-Asp-Trp-OH (SEQ ID NO:26),
Pro-Ser-Leu-Gly-Asp-Trp-OH (SEQ ID NO:27), Pro-Ser-Leu-Sar-Asp-Trp-OH (SEQ ID NO:28),
Pro-Ser-Leu-Ala-Asp-Trp-OH (SEQ ID NO:29), Pro-Ser-Leu-Gly-Asp-Phe-OH (SEQ ID NO:30),
Pro-Ser-Ile-Gly-Asp-Trp-OH (SEQ ID NO:31), Pro-Ser-Ile-Sar-Asp-Trp-OH (SEQ ID NO:32),
Pro-Ser-Ile-Ala-Asp-Trp-OH (SEQ ID NO:33)and Pro-Ser-(allo)Ile-Gly-Asp-Trp-OH (SEQ ID NO:34).

More preferred examples include:
Pro-Ser-Tle-Gly-Asp-Trp-OH (SEQ ID NO:19), Pro-Ser-Leu-Gly-Asp-Trp-OH (SEQ ID NO:27),
Pro-Ser-Ile-Gly-Asp-Trp-OH (SEQ ID NO:31)and Pro-Ser-(allo)Ile-Gly-Asp-Trp-OH (SEQ ID NO:34).

The most preferred examples include Pro-Ser-Tle-Gly-Asp-Trp-OH (SEQ ID NO:19).

In the case where the side chain in amino acid A is an aryl group, it includes phenyl and naphthyl groups and the like. The aryl group may be substituted with the above-mentioned group without electric charges such as an alkyl having 1-10 carbon atoms, a cycloalkyl having 3-10 carbon atoms or an aryl group, a halogen atom such as bromine, iodine, or chlorine atom or the like, a cyano, a nitro, an alkoxy having 1-10 carbon atoms, an acyl group having 2-10 carbon atoms or a keto group.

Examples of the neutral amino acids having an aryl group at a side chain include phenylglycine, naphthyl glycine and the like. Preferred examples include Pro-Ser-Phg-Gly-Asp-Trp-OH (SEQ ID NO:35)and the like.

In the case where the side chain in amino acid A is a heteroaryl group, it includes furyl, tetrahydrofuryl, pyranyl, thienyl groups and the like. The heteroaryl group may be substituted with the above-mentioned group without electric charges such as an alkyl having 1-10 carbon atoms, a cycloalkyl having 3-10 carbon atoms or an aryl group, a halogen atom such as bromine, iodine, or chlorine atom or the like, a cyano, a nitro, an alkoxy having 1-10 carbon atoms, an acyl group having 2-10 carbon atoms or a keto group.

In the case where the side chain in amino acid A is a cycloalkyl group having 3-10 carbon atoms, it is preferably a cycloalkyl group having an alkyl group having 3-7 carbon atoms such as a cyclopentyl, a cyclohexyl, a cycloheptyl group or the like. The cycloalkyl group may be substituted with the above-mentioned group without electric charges such as an alkyl having 1-10 carbon atoms, a cycloalkyl having 3-10 carbon atoms or an aryl group, a halogen atom such as bromine, iodine, or chlorine atom or the like, a cyano, a nitro, an alkoxy having 1-10 carbon atoms, an acyl group having 2-10 carbon atoms, a keto or a hydroxy group.

Examples of the neutral amino acids having a cycloalkyl group at a side chain include cyclohexyl glycine and the like. Preferred examples include Pro-Ser-Chg-Gly-Asp-Trp-OH (SEQ ID NO:36).

Specific examples of the groups in which the alkyl having 1-10 carbon atoms, aryl and heteroaryl groups, and cycloalkyl groups having 3-10 carbon atoms are combined include aralkyl groups such as phenyl alkyl groups; cycloalkyl-alkyl groups such as cyclohexyl alkyl groups; alkyl-cycloalkyl groups and the like. More specific examples include a benzyl, phenyl ethyl, cyclohexyl methyl groups and the like. The ring portion in the combined groups may be substituted with the above-mentioned group without electric charges such as an alkyl having 1-10 carbon atoms, a cycloalkyl having 3-10 carbon atoms or an aryl group, a halogen atom such as bromine, iodine, or chlorine atom or the like, a cyano, a nitro, an alkoxy having 1-10 carbon atoms, an acyl group having 2-10 carbon atoms, a keto or a hydroxy group.

Examples of the neutral amino acids having the above-mentioned combined groups include phenyl alanine, cyclohexyl alanine, 4-methylphenyl alanine, 4-bromophenyl alanine, naphthyl alanine, homophenyl alanine, and 0-methyl tyrosine. Preferred examples of the peptides include: Pro-Ser-Cha-Gly-Asp-Trp-OH (SEQ ID NO:37), Pro-Ser-Phe-Gly-Asp-Trp-OH (SEQ ID NO:38), and Pro-Ser-Hph-Gly-Asp-Trp-OH (SEQ ID NO:39).

More preferred examples include Pro-Ser-Cha-Gly-Asp-Trp-OH (SEQ ID NO:37).

In the case where the side chain in amino acid A is an alkyl, an aryl, a heteroaryl or a cycloalkyl group having a group without electric charges which contains a hetero atom such as oxygen, sulfur or the like, or a group in which these groups are combined, specific examples of such groups include alkyl and cycloalkyl groups having a hydroxy or a mercapto group, or an alkylthio group having 1-10 carbon atoms. Preferred examples of the neutral amino acids having such groups include serine, threonine, methionine, cysteine, homocysteine and the like.

In the case where amino acid A is an N-alkyl glycine having an alkyl group with 1-10 carbon atoms, one having an alkyl group with 3 or less carbon atoms such as sarcosine is preferred.

In the case where amino acid A is a proline having a substituent in its ring, exemplary substituents include the above-mentioned group without electric charges such as an alkyl having 1-10 carbon atoms, a cycloalkyl having 3-10 carbon atoms or an aryl group, a halogen atom such as bromine, iodine, or chlorine atom or the like, a cyano, a nitro, an alkoxy having 1-10 carbon atoms, an acyl group having 2-10 carbon atoms, a keto or a hydroxy group. Examples of the derivatives having an unsaturated bond include dehydroproline. Examples of the derivatives in which a ring-constituting carbon atom is substituted with a hetero atom include thioproline and the like. Preferred examples of the derivatives having different ring sizes include derivatives having from a 3-membered to an 8-membered ring such as azetidine-carboxylic acid, homoproline and the like. The proline derivatives may be combinations of them such as β,β-dimethyl thioproline and the like.

Examples of the neutral amino acids that provide peptides with high solubility and activities include serine, threonine, proline, hydroxyproline, dehydroproline, 4-methyl proline and 4-methoxy proline. Preferred examples of the peptides include:
Pro-Ser-Pro-Gly-Asp-Trp-OH (SEQ ID NO:40), Pro-Ser-Pro-Sar-Asp-Trp-OH (SEQ ID NO:41),
Pro-Ser-Pro-Ala-Asp-Trp-OH (SEQ ID NO:42), Pro-Ser-Ser-Gly-Asp-Trp-OH (SEQ ID NO:43),
Pro-Ser-Ser-Sar-Asp-Trp-OH (SEQ ID NO:44), Pro-Ser-Thr-Gly-Asp-Trp-OH (SEQ ID NO:45),
Pro-Ser-Thr-Sar-Asp-Trp-OH (SEQ ID NO:46), Pro-Ser-Hyp-Gly-Asp-Trp-OH (SEQ ID NO:47),
Pro-Ser-Hyp-Sar-Asp-Trp-OH (SEQ ID NO:48), Pro-Ser-ΔPro-Gly-Asp-Trp-OH (SEQ ID NO:49),
Pro-Ser-ΔA Pro-Sar-Asp-Trp-OH (SEQ ID NO:50), Pro-Ser-(4-CH$_3$ Pro)-Gly-Asp-Trp-OH (SEQ ID NO:51),
Pro-Ser-(4-CH$_3$Pro)-Sar-Asp-Trp-OH (SEQ ID NO:52), Pro-Ser-(4-OCH$_3$ Pro)-Gly-Asp-Trp-OH (SEQ ID NO:53),
Pro-Ser-(4-OCH$_3$ Pro)-Sar-Asp-Trp-OH (SEQ ID NO:54), Pro-Ser-Thz-Gly-Asp-Trp-OH (SEQ ID NO:55),
Pro-Ser-Dmt-Gly-Asp-Trp-OH (SEQ ID NO:56), Pro-Ser-Dmp-Gly-Asp-Trp-OH (SEQ ID NO:57),
Pro-Ser-Azt-Gly-Asp-Trp-OH (SEQ ID NO:58) and Pro-Ser-Hyp(Bzl)-Gly-Asp-Trp-OH (SEQ ID NO:59).

More preferred examples include:
Pro-Ser-Pro-Gly-Asp-Trp-OH (SEQ ID NO:40), Pro-Ser-Hyp-Gly-Asp-Trp-OH (SEQ ID NO:47),
Pro-Ser-ΔA Pro-Gly-Asp-Trp-OH (SEQ ID NO:49) and Pro-Ser-Hyp(Bzl)-Gly-Asp-Trp-OH (SEQ ID NO:59).

The most preferred examples include Pro-Ser-ΔA Pro-Gly-Asp-Trp-OH (SEQ ID NO:49).

D-amino acids can be used in order to prevent the enzymatic breakdown and to maintain the high activities of the peptides. Preferred examples of the D-amino acids include D-isomers of the above-mentioned neutral amino acids and preferred examples of the peptides include Pro-Ser-DPro-Gly-Asp-Trp-OH (SEQ ID NO:60).

Examples of the amino acids having at a side chain an amino group which may be substituted with an alkyl group having 1–10 carbon atoms include amino acid residues represented by the following general formula (X):

wherein $R^1$ and $R^2$ which may be the same or different are each a hydrogen atom or an alkyl group having 1–10 carbon atoms, and n is an integer of 4–10. Preferred examples include amino acid residues represented by the following general formula (X'):

wherein $R^1$ is a hydrogen atom, a methyl or t-butyl 9group. These amino acid residues are lysine, ε-N-methyllysine and ε-N-t-butyllysine residues. Lysine is preferred to ε-N-methyllysine and ε-N-methyllysine is preferred to ε-N-t-butyllysine residues in terms of their steric hindrance. Lysine having an unsubstituted amino group is preferred. As shown in Experimental Example 1 to be described later, peptides containing lysine as amino acid A (a compound prepared in Example 13 with n in the above formula (X) being 4) exhibit higher platelet aggregation-inhibiting and blood coagulation-inhibiting activities than peptides containing ornithine as amino acid A (a compound with n=3 prepared in Comparative Example 1). The integer n in the formula (X) represents the distance from α-carbon to an amino acid at a side chain. Hence, n is preferably at least 4, more preferably 4–6.

Moreover, in addition to the above-mentioned facts, as shown in Experimental Example 1 to be described later, peptides containing norvaline as amino acid A which has an alkyl chain of the same length at a side chain but which does not have a basic functional amino group (a compound prepared in Example 4) exhibit remarkably enhanced platelet aggregation-inhibiting and blood coagulation-inhibiting activities, compared with peptides containing ornithine as amino acid A (a compound prepared in Comparative Example 1).

In general formula (I), B is an amino acid. Amino acids having great steric hindrance and acidic amino acids tend to reduce the platelet aggregation-inhibiting and blood coagulation-inhibiting activities of peptides containing them. Hence, preferred examples of the amino acid B include neutral amino acids having a relatively small side chain having 10 or less carbon atoms and N-alkyl substitution products thereof. The carbon number of the alkyl group in the N-alkyl substitution products is preferably 1–5. Specifically, glycine, alanine, β-alanine, sarcosine, N-ethyl glycine, N-isopropyl glycine, N-propyl glycine and the like may be mentioned as preferred examples. As shown in Experimental Example 1 to be described later, the peptides of the present invention containing, as B, sarcosine (a compound prepared in Example 1) exhibit about twice as much platelet aggregation-inhibiting and blood coagulation-inhibiting activities as peptides containing glycine as B (a compound prepared in Example 2). It is believed that this is because the main chains of peptides generally have trans configuration, but they change into a cis-form when sarcosine is introduced and these structures contribute to form the configurations required for higher platelet aggregation-inhibiting and blood coagulation-inhibiting activities.

Any amino acid having a hydrophobic group at a side chain that interacts with a receptor through a hydrophobic bond can be used as C in general formula (I). Preferred examples of the amino acid as C include amino acids having a hydrophobic group such as an alkyl, a phenyl, a phenylalkyl, an alkoxyphenyl, a cycloalkyl, a pyridyl, an indolyl group or the like at a side chain. Specific examples include phenyl alanine, tryptophan, O-alkyl tyrosine, naphthyl alanine, pyridyl alanine and the like. Among them, tryptophan is preferred. As the alkyl group, lower alkyl groups having no more than 10 carbon atoms are preferred.

In general formual (I), D is a hydroxy or an amino group. In the case where D is a hydroxy group, the activities of peptides tend to become higher than when D is an amino group. However, the working time is longer in the case where D is an amino group. The selection of a hydroxy or an amino group depends on the purpose of interest.

When amino acids, peptides, protective groups, active groups and the like are designated herein by abbreviations, they should comply with the definition by IUPAC and IBU or any conventional symbols used in the art. In the case where an α-amino acid directly related to genetic control can have optical isomerism, it is to be understood that an L-isomer is meant unless otherwise indicated.

Examples of the abbreviations are shown below.

Asp or D: Aspartic acid
Ala : Alanine
Arg or R: Arginine
Gly or G: Glycine
Phg: Phenylglycine
Sar: Sarcosine
Ser or S: Serine
Thr: Threonine
Val: Valine
Nva: Norvaline
Ile: Isoleucine
(allo)Ile: allo Isoleucine
Leu: Leucine
Nle: Norleucine
Tle: Tertiary leucine
Lys: Lysine
Chg: Cyclohexyl glycine
Cha: Cyclohexyl alanine
Met: Methionine
Trp: Tryptophan
Tyr: Tyrosine
Tyr (CH$_3$): O-Methyl tyrosine
Phe or F: Phenylalanine
Hph: Homophenylalanine
Pro or P: Proline
DPro: D-Proline
Hyp: Hydroxyproline
Δ Pro: Dehydroproline
4-CH$_3$ Pro: 4-Methyl proline
4-OCH$_3$ Pro: 4-Methoxy proline
Boc: t-Butoxycarbonyl
Bu$^t$: t-Butyl
OBu$^t$: t-Butyl ester Mtr: 4-Methoxy-2,3,6-trimethyl benzene sulfonyl
$P_{mc}$: 2,2,5,7,8-pentamethylchroman-6-sulfonyl
$F_{mo\ c}$: 9-Fluorenyl methoxycarbonyl
Orn: Ornithine
Cys: Cysteine
Pen: Penicillamine
Azt: Azetidine-carboxylic acid
Thz: Thioproline
Dmt: Dimethyl thioproline
Dmp: Dimethyl proline The peptides of the present invention can be easily synthesized with commercially available amino acids by simple procedures. For example, they can be prepared either in a liquid or solid phase by a conventional method used in peptide chemistry such as ones described in Schroder and Luhke, "The Peptides" vol.1, Academic Press, New York, U.S.A. (1966), Nobuo Izumiya et al., "The Fundamentals and Experiments of Peptide Synthesis", Maruzen (1985) and the like. These preparation methods may be a column or batch method.

The condensation methods for forming peptide bonds include the azide method, acid chloride method, acid anhydride method, carbodiimide method, carbodiimide-additive method, active ester method, carbonyl imidazole method, redox method, enzymic method, the method using Woodward's reagent K and the like. In the case of performing a condensation reaction by a solid phase method, the acid anhydride method, carbodiimide method and active ester method may predominantly be used.

When a peptide chain is elongated by the solid phase method, the C-terminal amino acid is coupled to a support such as a resin that is insoluble in the organic solvents to be used. In this case, the resin may be modified depending on the purpose by introducing a functional group for the purpose of bonding amino acids to the resin, by inserting a spacer between the resin and a functional group or by introducing a chain called "handle" which can be cleaved in various positions depending on the conditions. Exemplary resins include halomethyl resins (such as chloromethyl resin), oxymethyl resin, 4-(oxymethyl)-phenylacetamide methyl resin, 4-(oxymethyl)-phenoxymethyl resin, resin for C-terminal amidation and the like.

Prior to the condensation reaction, carboxyl and amino groups, and guanidino group in arginine residue that do not take part in the condensation reaction may be protected by conventional and known techniques. In contrast with this, carboxyl and amino groups that directly take part in the condensation reaction may be activated.

As protective groups for the protection, those which are commonly used in the field of organic chemistry, as described in Greene, "Protective Groups in Organic Synthesis", John Willey & Sons, Inc. (1981), can be used.

Exemplary protective groups for carboxyl group include commonly used and known protective groups such as various kinds of methyl ester, ethyl ester, benzyl ester, p-nitrobenzyl ester, t-butyl ester, cyclohexyl ester and the like.

Exemplary protective groups for amino group include benzyl oxycarbonyl, t-butoxycarbonyl, isobornyloxycarbonyl and 9-fluorenyl methoxycarbonyl groups and the like.

Exemplary protective groups for hydroxy group in an amino acid residue such as serine include t-butyl, benzyl, trimethylsilyl and tetrahydropyranyl groups and the like.

Exemplary protective groups for ε-amino group in lysine includet-butoxycarbonyl, 9-fluorenylmethoxycarbonyl groups and the like.

Exemplary amino acids with an activated carboxyl group include the acid anhydride corresponding to the carboxyl group; azide; active esters with pentafluorophenol, 2,4-dinitrophenol, cyanomethyl alcohol, p-nitrophenol, N-hydroxysuccinimide, N-hydroxy-5-norbornene-2,3-dicarboximide, N-hydroxyphthalimide, and 1-hydroxybenzotriazole and the like.

Exemplary amino acids with an activated amino group include amide phosphate corresponding to the amino group.

The condensation reaction for peptide synthesis is usually carried out in a solvent. Exemplary solvents include chloroform, dichloromethane, ethyl acetate, N,N-dimethylformamide, dimethyl sulfoxide, pyridine, dioxane, tetrahydrofuran, N-methyl pyrrolidone, water, methanol and the like, and a mixture thereof. In general, the condensation reaction can be carried out at a temperature of from +30°to 50° C. as usual.

The kind of the deprotection reaction of the protective groups in the peptide preparation process can be selected depending on the kind of the protective groups, provided that the protective groups can be eliminated without affecting the peptide bonds. Exemplary deprotection reactions include a treatment with an acid such as hydrogen chloride, hydrogen bromide, anhydrous hydrogen fluoride, methanesulfonic acid, trifluoromethanesulfonic acid, trifluoro acetic acid, or a mixture thereof; a treatment with an alkali such as sodium hydroxide, potassium hydroxide, hydrazine, diethylamine, piperidine, or the like; a treatment with sodium in liquid ammonia; reduction with palladium on carbon; a silylation treatment with trimethylsilyl triflate, trimethylsilyl bromide or the like. In the above deblocking reaction with an acid or silylation agent, cation-trapping agents such as anisole, phenol, cresol, thioanisole and ethanedithiol are preferably added to carry out the deblocking reaction effectively.

The peptides synthesized by the solid phase method can be cleaved from the solid phase by conventional methods. Exemplary methods for cleaving the peptide include treatments with the acid or silylation agent described above.

The peptides thus prepared can be separated and purified in a conventional and known manner after the end of the series of reactions described above. For example, extraction, partition, reprecipitation, recrystallization, column chromatography and the like can be used to obtain the peptides in a more purified form.

The peptides of the present invention may be obtained in salt forms depending upon the reaction conditions in the preparation processes. Exemplary salts include inorganic acid salts such as hydrochloride, sulfate, nitrate, phosphate and the like; organic acid salts such as formate, acetate, propionate, glycolate, succinate, malate, tartrate, citrate, trifluoroacetate and the like; alkaline metal salts such as sodium and potassium salt and the like; alkaline earth metal salts such as calcium salt and the like; organic amine salts such as an ammonium, ethanolamine, triethylamine and dicyclohexylamine salt, and the like.

When the peptides of the present invention thus prepared are used as active ingredients of platelet aggregation-inhibiting agents, cell adhesion-inhibiting agents, tumor metastasis-inhibiting agents, and protective agents for platelet preparations for blood transfusion (hereinafter referred to as "platelet aggregation-inhibiting agents and the like"), it is preferred that the peptides or pharmaceutically acceptable salts thereof are formulated together with a solid or liquid pharmaceutically acceptable carrier or diluent, that is, an excipient, stabilizer, etc to prepare pharmaceutical compositions. In the pharmaceutical compositions, the ratio of the active ingredient to the carrier can be varied in a range of 1 to 90% by weight. The pharmaceutical compositions may be orally administered in the form of granules, fine granules, powders, tablets, capsules, pills, liquids and solutions, and the like. Alternatively, the pharmaceutical compositions may be orally administered in the form of bulk powders or they can be administered intravenously, intramuscularly or subcutaneously as injections. The injections may be prepared just before use from powders of the peptides or pharmaceutically acceptable salts thereof of the present invention.

An organic or inorganic, solid or liquid pharmaceutically acceptable carrier or diluent suitable for oral, enteral or parenteral administration can be used to prepare the platelet aggregation-inhibiting agents and the like of the present invention. Water, gelatin, lactose, starch, magnesium stearate, talc, animal fats and oils, vegetable fats and oils, benzyl alcohol, gums, polyalkylene glycol, petroleum resins, coconut oil, lanolin, and all other carriers for medicines can be used as carriers or diluents for the platelet aggregation-inhibiting agents and the like of the present invention. Stabilizers, wetting agents, emulsifying agents, and salts for changing osmolarity or maintaining suitable pH of the preparation can be appropriately used as adjuvants.

If necessary, the platelet aggregation-inhibiting agents and the like of the present invention may contain other pharmaceutically active ingredients such as other kinds of platelet aggregation-inhibiting components in the case where they are used for the treatment of various diseases.

In the case of granules, fine granules, powders, tablets or capsules, the content of the active ingredient is preferably in the range from 5 to 80% by weight. In the case of liquids and solutions, the content of the active ingredient is preferably in the range from 1 to 30% by weight. Furthermore, in the case of injections, the content of the active ingredient is preferably in the range from 1 to 10% by weight.

When the platelet aggregation-inhibiting agents and the like are to be administered orally, the clinical dose of the active ingredient is preferably in the range from 500 to 1000 mg per day for adult patient, which can be varied depending on the age of the patient, severity of the disease to be treated and the like. The platelet aggregation-inhibiting agents and the like can be administered in the aforementioned daily dose either once a day, or twice or three times a day at suitable intervals. In the case of injections, the dose of the active ingredient is preferably in the range from one to several hundreds mg per injection for adult patient. Alternatively, the platelet aggregation-inhibiting agents and the like can be administered by a method such as instillation or the like in a single or several shots.

When the peptides or salts thereof of the present invention are used for extracorporeal circulation, they can be used in the form of injections and drip infusions. The position and dose of administration may be varied depending on the kind of extracorporeal circulation system, their duration time and the like. For example, the peptides can be injected or infused continuously in a dose of from 1 to 100 mg/kg per hour from the inlet to an extracorporeal circulation system. Irrespective of whether they are used singly or in combination with other drugs, the peptides are effective in a smaller dose in extracorporeal circulation systems than in vivo where degradation enzymes are present in large amounts.

It is believed that if the peptides of the present invention are combined with heparin which is used as a blood coagulation-inhibiting agent in the prior art, two important routes of blood coagulation, i.e., platelet aggregation and coagulation systems, are inhibited and thereby inhibit blood coagulation completely. In addition, since synergism of both kinds of drugs is expected, the use of heparin having the already described unwanted side effects can be reduced. Furthermore, the combinations of the peptides of the present invention with citric acid, protease-inhibiting agents such as futhan, fibrinolytic agents such as tissue plasminogen activator and the like are believed to be effective.

In the present invention, the form of the platelet preparation packs for blood transfusion are characterized in that the agents for protecting platelets for blood transfusion are contained in platelet preparations for blood transfusion, and are not particularly limited. All of the forms of platelet preparation packs for blood transfusion that are commonly used in clinical practice can be employed. Suitable examples include pack types bags, bottles and the like. The materials therefor also are not particularly limited. For example, poly-vinyl materials capable of inhibiting the adsorption of the active ingredient as much as possible, such as polyvinyl chloride, polyolefins and the like can be used as materials for the bags; plastic and glass materials can be used as materials for the bottles. The agents for protecting platelet preparations for blood transfusion of the present invention can be added at a final concentration of from 0.1µM to 1 mM, preferably from 1µM to 50 µM in terms of the amount of the peptides or salts thereof of the present invention based on the amount of platelet components. Of course, other components that are usually added to platelet preparation packs for blood transfusion can be added together with the agents of the present invention for protecting platelets for blood transfusion.

In addition, the peptides of the present invention can be used in preventing re-thrombosis after the thrombolytic treatment and thrombus formation after surgery by utilizing their characters such as potent platelet aggregation-inhibiting action and low toxicity. Specifically, the peptides of the present invention can be used in preventing blood restenosis after percutaneous transluminal coronary angioplasty (PTCA) which is performed by surgery against cardiac infarction and various other arterial thrombi, maintaining graft patency after angioplasty such as arterial or venous hemitransplant, preventing thrombus formation after the transplant of artificial blood vessels, and the like.

EXAMPLES

Figure 1:
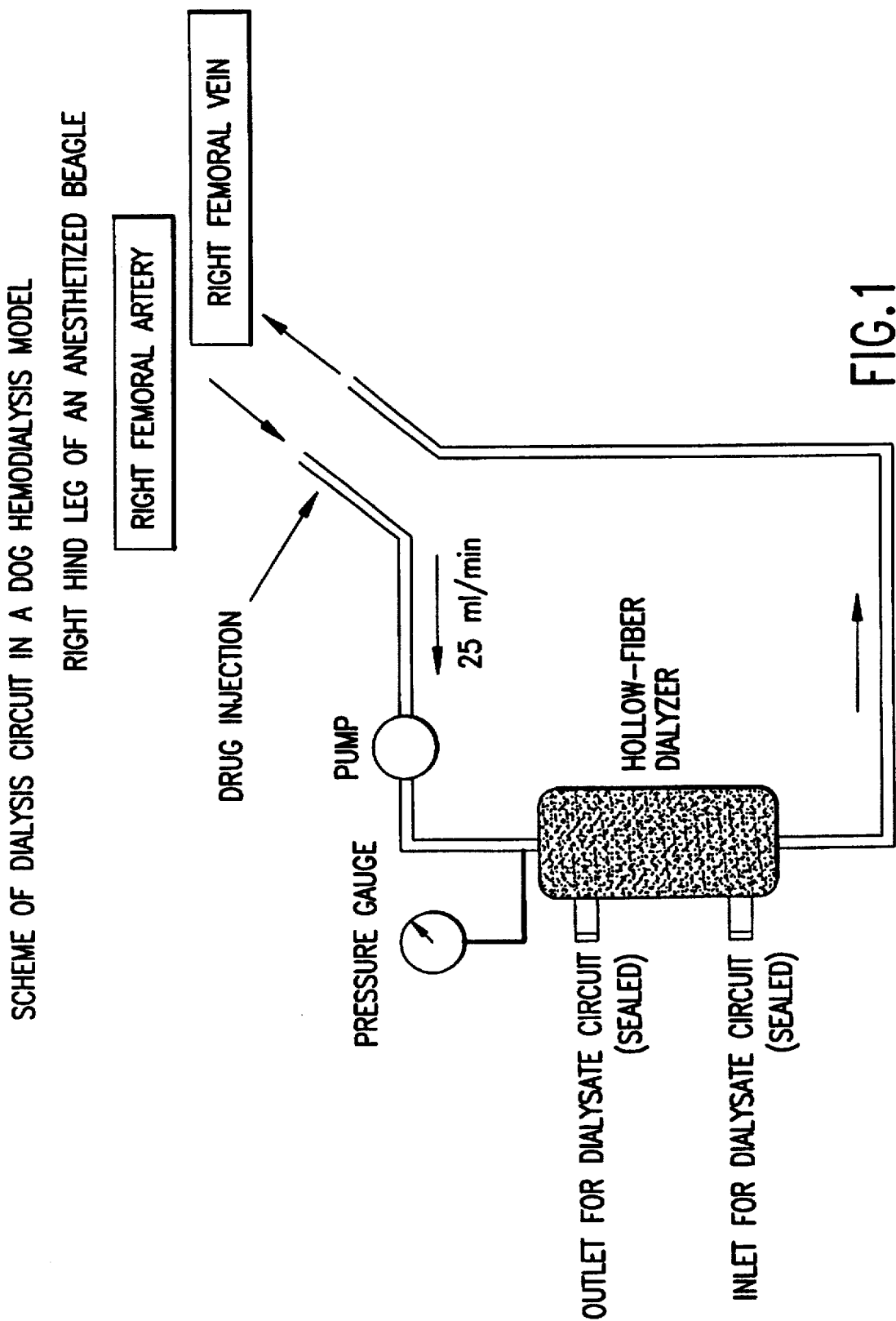
FIG. 1 is a scheme of a dialysis circuit in a dog hemodialysis model.

The present invention will be explained hereinafter in greater detail with reference to the following working examples.

[SYNTHESIS OF COMPOUNDS]

[Example 1]

Synthesis of Pro-Ser-Ala-Sar-Asp-Trp-OH (SEQ ID NO:8)

p-Alkoxybenzyl alcohol-type resin represented by the following formula (the amount of Trp introduced: 0.87 meq/g; BACHEM Co.) (0.275 g; 0.25 mmol)

HOCH$_2$—C$_6$H$_4$ (1,4)—OCH$_2$—C$_6$H$_4$ (1,4) -Polymer was placed in a reaction container. F$_{mo\ c}$-Trp was introduced in the form of active ester in the presence of dimethyaminopyrimidine and thereafter shaking and filtering steps were repeated as listed in Table 1 to obtain a protected peptide resin represented by the following general formula.

Pro-Ser(Bu$^t$)-Ala-Sar-Asp(OBu$^t$)-Trp-Resin

The obtained protected peptide resin was treated with thioanisole in the presence of m-cresol and ethanedithiol in trifluoroacetic acid (TFA) at 0° C. for one hour. TFA was distilled off with an evaporator and thereafter the resin was removed by filtration. Diethyl ether was added to the filtrate under ice-cooling to obtain a peptide cleaved from the resin as a powder. The powder was washed with diethyl ether. The washed peptide was desalted by gel permeation chromatography using Sephadex G-10 (Pharmacia Co. ) as a support and lyophilized to obtain a crude peptide. The crude peptide was purified by high pressure liquid chromatography (HPLC) (column: ODS 5C$_{18}$(ebondasphere, φ20×150 mm), mobile phase: (A) 0.1% TFA, (B) 100% CH$_3$CN/0.1% TFA, gradient: (A):(B)=90:10 to (A):(B)=70:30, 20 minutes, flow rate: 17 ml/min). The acetate of the peptide was obtained by gel filtration using Sephadex G-25 (Pharmacia Co.) as a support and lyophilized to obtain 34 mg of the titled peptide. Amino acid analysis (6N HCl+phenol, 24 hr, 110° C.)

In this assay, tryptophan cannot be detected because it is degraded during acid hydrolysis. Amino acids whose standards are not present cannot be detected because amino acids used as external standards for the determination are standard amino acids.

| Asp | 1.06 (1) |
| Ser | 1.00 (1) |
| Sar | — (1) |
| Trp | — (1) |
| Ala | 1.09 (1) |
| Pro | 1.10 (1) |

HPLC analysis

A spectrum of analytical HPLC using Cosmosil 5C18-AR (φ4.6×200 mm) column (Nacalai tesque Co.) at a flow rate of 1.0 ml/min by elution in a gradient of acetonitrile of 10–40% (60 min) in 0.1% TFA indicated a single peak at a retention time of 18.0 minutes.

FAB-MS: M+H Calculated 646.3, Found 646

TABLE 1

| Steps | Reagents or Solvents | Amounts of use (ml/step) | Time (minute) | The number of Times |
|---|---|---|---|---|
| 1. | DMF | 30 | 1 | 6 |
| 2. | 20% Piperidine/DMF | 6 | 2 | 1 |
| 3. | 20% Piperidine/DMF | 6 | 20 | 1 |
| 4. | DMF | 50 | 1 | 10 |
| 5. | F$_{mo\ c}$-amino-acid & HOBT**/DMF (3 eq each) | 6 | 2* | 1 |
| 6. | DIPCD** (3 eq)*** | 6 | 120 | 1 |

*: proceed to the next step without removing the reagent or solvent after shaking.
**: 1-Hydroxybenzotriazole
***: Diisopropylcarbodiimide

[Example 2]

Synthesis of Pro-Ser-Ala-Gly-Asp-Trp-OH (SEQ ID NO:7)

The titled peptide was synthesized by the same procedure as in Example 1.

| Amino acid analysis (6N HCl + phenol, 24 hr, 110° C.) | |
|---|---|
| Asp | 0.82 (1) |
| Ser | 1.00 (1) |
| Gly | 1.08 (1) |
| Trp | — (1) |
| Ala | 1.08 (1) |
| Pro | 1.19 (1) |

HPLC analysis

A spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 19.2 minutes.

FAB-MS: M+H Calculated 632.3, Found 632

[Example 3]

Synthesis of Pro-Ser-Val-Sar-Asp-Trp-OH (SEQ ID NO:25)

The titled peptide was synthesized by the same procedure as in Example 1.

| Amino acid analysis (6N HCl + phenol, 24 hr, 110° C.) | |
|---|---|
| Asp | 0.99 (1) |
| Ser | 1.00 (1) |
| Sar | — (1) |
| Trp | — (1) |
| Val | 1.13 (1) |
| Pro | 1.01 (1) |

HPLC analysis

A spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 20.0 minutes.

FAB-MS: M+H Calculated 674.3, Found 674

[Example 4]

Synthesis of Pro-Ser-Nva-Gly-Asp-Trp-OH (SEQ ID NO:1)

The titled peptide was synthesized by the same procedure as in Example 1.

| Amino acid analysis (6N HCl + phenol, 24 hr, 110° C.) | |
|---|---|
| Asp | 1.03 (1) |
| Ser | 1.00 (1) |
| Gly | 1.12 (1) |
| Trp | — (1) |
| Nva | 1.08 (1) |
| Pro | 1.21 (1) |

HPLC analysis

A spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 26.0 minutes.

FAB-MS: M+H Calculated 660.3, Found 660

[Example 5]

Synthesis of Pro-Ser-Nva-Sar-Asp-Trp-OH (SEQ ID NO:2)

The titled peptide was synthesized by the same procedure as in Example 1.

| Amino acid analysis (6N HCl + phenol, 24 hr, 110° C.) | |
|---|---|
| Asp | 0.97 (1) |
| Ser | 1.00 (1) |
| Sar | — (1) |
| Trp | — (1) |
| Nva | 1.12 (1) |
| Pro | 1.24 (1) |

HPLC analysis

A spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 28.5 minutes.
FAB-MS: M+H Calculated 674.3, Found 674

[Example 6]

Synthesis of Pro-Ser-Leu-Gly-Asp-Trp-OH (SEQ ID NO:27)

The titled peptide was synthesized by the same procedure as in Example 1.

| Amino acid analysis (6N HCl + phenol, 24 hr, 110° C.) | |
|---|---|
| Asp | 0.97 (1) |
| Ser | 1.00 (1) |
| Gly | 1.12 (1) |
| Trp | — (1) |
| Leu | 1.16 (1) |
| Pro | 1.08 (1) |

HPLC analysis

A spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 32.0 minutes.
FAB-MS: M+H Calculated 674.3, Found 674

[Example 7]

Synthesis of Pro-Ser-Leu-Sar-Asp-Trp-OH (SEQ ID NO:28)

The titled peptide was synthesized by the same procedure as in Example 1.

| Amino acid analysis (6N HCl + phenol, 24 hr, 110° C.) | |
|---|---|
| Asp | 1.01 (1) |
| Ser | 1.00 (1) |
| Sar | — (1) |
| Trp | — (1) |
| Leu | 1.07 (1) |
| Pro | 1.13 (1) |

HPLC analysis

A spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 36.0 minutes.
FAB-MS: M+H Calculated 688.3, Found 688

[Example 8]

Synthesis of Pro-Ser-Nle-Sar-Asp-Trp-OH (SEQ ID NO:5)

The titled peptide was synthesized by the same procedure as in Example 1.

| Amino acid analysis (6N HCl + phenol, 24 hr, 110° C.) | |
|---|---|
| Asp | 0.97 (1) |
| Ser | 1.00 (1) |
| Sar | — (1) |
| Trp | — (1) |
| Nle | 1.22 (1) |
| Pro | 1.10 (1) |

HPLC analysis

A spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 34.5 minutes.
FAB-MS: M+H Calculated 688.3, Found 688

[Example 9]

Synthesis of Pro-Ser-Nle-Gly-Asp-Trp-OH (SEQ ID NO:4)

The titled peptide was synthesized by the same procedure as in Example 1.

| Amino acid analysis (6N HCl + phenol, 24 hr, 110° C.) | |
|---|---|
| Asp | 0.94 (1) |
| Ser | 0.94 (1) |
| Gly | 1.04 (1) |
| Trp | — (1) |
| Nle | 1.06 (1) |
| Pro | 1.00 (1) |

HPLC analysis

A spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 34.6 minutes.
FAB-MS: M+H Calculated 674.3, Found 674

[Example 10]

Synthesis of Pro-Ser-Ala-Sar-Asp-Phe-OH (SEQ ID NO:10)

The titled peptide was synthesized by the same procedure as in Example 1.

| Amino acid analysis (6N HCl + phenol, 24 hr, 110° C.) | |
|---|---|
| Asp | 1.09 (1) |
| Ser | 0.93 (1) |
| Sar | — (1) |
| Phe | 1.08 (1) |
| Ala | 1.00 (1) |
| Pro | 1.03 (1) |

HPLC analysis

A spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 17.0 minutes.
FAB-MS: M+H Calculated 607.3, Found 607

[Example 11]

Synthesis of Pro-Ser-Gly-Sar-Asp-Trp-OH (SEQ ID NO:12)

The titled peptide was synthesized by the same procedure as in Example 1.

| Amino acid analysis (6N HCl + phenol, 24 hr, 110° C.) | |
|---|---|
| Asp | 1.07 (1) |
| Ser | 1.00 (1) |
| Gly | 1.14 (1) |
| Trp | — (1) |
| Sar | — (1) |
| Pro | 1.10 (1) |

HPLC analysis spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 18.0 minutes.
FAB-MS: M+H Calculated 632.3, Found 632

[Example 12]

Synthesis of Pro-Ser-Ile-Sar-Asp-Trp-OH (SEQ ID NO:32)

The titled peptide was synthesized by the same procedure as in Example 1.

| Amino acid analysis (6N HCl + phenol, 24 hr, 110° C.) | |
|---|---|
| Asp | 0.99 (1) |
| Ser | 1.00 (1) |
| Sar | — (1) |
| Trp | — (1) |
| Ile | 1.20 (1) |
| Pro | 1.18 (1) |

HPLC analysis spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 34.0 minutes.
FAB-MS: M+H Calculated 688.3, Found 688

[Example 13]

Synthesis of Pro-Ser-Lys-Gly-Asp-Trp-OH (SEQ ID NO:61)

The titled peptide was synthesized by the same procedure as in Example 1.

| Amino acid analysis (6N HCl + phenol, 24 hr, 110° C.) | |
|---|---|
| Asp | 0.99 (1) |
| Ser | 1.00 (1) |
| Gly | 1.19 (1) |
| Trp | — (1) |
| Lys | 1.15 (1) |
| Pro | 1.24 (1) |

HPLC analysis spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 17.0 minutes.
FAB-MS: M+H Calculated 689.3, Found 689

[Example 14]

Synthesis of Pro-Ser-Ile-Gly-Asp-Trp-OH (SEQ ID NO:31)

The titled peptide was synthesized by the same procedure as in Example 1.

| Amino acid analysis (6N HCl + phenol, 24 hr, 110° C.) | |
|---|---|
| Asp | 0.98 (1) |
| Ser | 1.00 (1) |
| Gly | 1.08 (1) |
| Trp | — (1) |
| Ile | 1.05 (1) |
| Pro | 1.12 (1) |

HPLC analysis spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 34.2 minutes.
FAB-MS: M+H Calculated 674.3, Found 674

[Example 15]

Synthesis of Pro-Ser-Ser-Gly-Asp-Trp-OH (SEQ ID NO:43)

The titled peptide was synthesized by the same procedure as in Example 1.

| Amino acid analysis (6N HCl + phenol, 24 hr, 110° C.) | |
|---|---|
| Asp | 1.01 (1) |
| Ser | 2.00 (2) |
| Gly | 1.15 (1) |
| Trp | — (1) |
| Pro | 1.10 (1) |

HPLC analysis

A spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 19.0 minutes.
FAB-MS: M+H Calculated 648.3, Found 648

[Example 16]

Synthesis of Pro-Ser-Nva-Gly-Asp-Phe-OH (SEQ ID NO:62)

The titled peptide was synthesized by the same procedure as in Example 1.

| Amino acid analysis (6N HCl + phenol, 24 hr, 110° C.) | |
|---|---|
| Asp | 1.01 (1) |
| Ser | 1.00 (1) |
| Gly | 1.10 (1) |
| Nva | 1.12 (1) |
| Phe | 0.98 (1) |
| Pro | 1.05 (1) |

HPLC analysis spectrum of analytical HPLC using Cosmosil 5C18-AR (φ4.6×200 mm) column (Nakalai tesque Co.) at a flow rate of 1.0 ml/min by elution in a gradient of acetonitrile of 10–40% (60 min) in 0.1% TFA indicated a single peak at a retention time of 30.2 minutes.
FAB-MS: M+H Calculated 621.3, Found 621

[Example 17]

Synthesis of Pro-Ser-Nva-Gly-Asp-Hph-OH (SEQ ID NO:63)

The titled peptide was synthesized by the same procedure as in Example 1.

| Amino acid analysis (6N HCl + phenol, 24 hr, 110° C.) | |
|---|---|
| Asp | 0.97 (1) |
| Ser | 1.00 (1) |
| Gly | 1.12 (1) |
| Nva | 1.09 (1) |
| Hph | 1.11 (1) |
| Pro | 1.06 (1) |

HPLC analysis spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 31.5 minutes.

FAB-MS: M+H Calculated 635.3, Found 635

[Example 18]

Synthesis of Pro-Ser-Nva-Gly-Asp-Tyr(CH$_3$)-OH (SEQ ID NO:64)

The titled peptide was synthesized by the same procedure as in Example 1.

| Amino acid analysis (6N HCl + phenol, 24 hr, 110° C.) | |
|---|---|
| Asp | 0.99 (1) |
| Ser | 1.00 (1) |
| Gly | 1.08 (1) |
| Nva | 1.17 (1) |
| Tyr(CH$_3$) | 1.05 (1) |
| Pro | 1.12 (1) |

HPLC analysis spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 27.6 minutes.

FAB-MS: M+H Calculated 651.3, Found 651

[Example 19]

Synthesis of Pro-Ser-Pro-Gly-Asp-Trp-OH (SEQ ID NO:40)

The titled peptide was synthesized by the same procedure as in Example 1.

| Amino acid analysis (6N HCl + phenol, 24 hr, 110° C.) | |
|---|---|
| Asp | 0.99 (1) |
| Ser | 1.00 (1) |
| Gly | 1.08 (1) |
| Trp | — (1) |
| Pro | 2.13 (2) |

HPLC analysis spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 21.0 minutes.

FAB-MS: M+H Calculated 658.3, Found 658

[Example 20]

Synthesis of Pro-Ser-(allo)Ile-Gly-Asp-Trp-OH (SEQ ID NO:34)

The titled peptide was synthesized by the same procedure as in Example 1.

| Amino acid analysis (6N HCl + phenol, 24 hr, 110° C.) | |
|---|---|
| Asp | 0.97 (1) |
| Ser | 1.00 (1) |
| Gly | 1.07 (1) |
| (allo)Ile | 1.08 (1) |
| Trp | — (1) |
| Pro | 1.12 (1) |

HPLC analysis

A spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 32.1 minutes.

FAB-MS: M+H Calculated 674.3, Found 674

[Example 21]

Synthesis of Pro-Ser-Tle-Gly-Asp-Trp-OH (SEQ ID NO:19)

The titled peptide was synthesized by the same procedure as in Example 1.

| Amino acid analysis (6N HCl + phenol, 24 hr, 110° C.) | |
|---|---|
| Asp | 0.99 (1) |
| Ser | 1.00 (1) |
| Gly | 1.05 (1) |
| Tle | 1.02 (1) |
| Trp | — (1) |
| Pro | 1.10 (1) |

HPLC analysis spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 34.0 minutes.

FAB-MS: M+H Calculated 674.3, Found 674

[Example 22]

Synthesis of Pro-Ser-Chg-Gly-Asp-Trp-OH (SEQ ID NO:36)

The titled peptide was synthesized by the same procedure as in Example 1.

| Amino acid analysis (6N HCl + phenol, 24 hr, 110° C.) | |
|---|---|
| Asp | 1.01 (1) |
| Ser | 1.00 (1) |
| Gly | 0.99 (1) |
| Chg | 1.08 (1) |
| Trp | — (1) |
| Pro | 1.05 (1) |

HPLC analysis spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 39.5 minutes.

FAB-MS: M+H Calculated 700.3, Found 700

[Example 23]

Synthesis of Pro-Ser-Met-Gly-Asp-Trp-OH (SEQ ID NO:14)

The titled peptide was synthesized by the same procedure as in Example 1.

| Amino acid analysis (6N HCl + phenol, 24 hr, 110° C.) | |
|---|---|
| Asp | 1.00 (1) |
| Ser | 1.00 (1) |
| Gly | 1.06 (1) |
| Met | 1.09 (1) |
| Trp | — (1) |
| Pro | 1.02 (1) |

HPLC analysis spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 29.0 minutes.
FAB-MS: M+H Calculated 692.4, Found 692

[Example 24]

Synthesis of Pro-Ser-Nva-Gly-Asp-Cha-OH (SEQ ID NO:65)

The titled peptide was synthesized by the same procedure as in Example 1.

| Amino acid analysis (6N HCl + phenol, 24 hr, 110° C.) | |
|---|---|
| Asp | 1.03 (1) |
| Ser | 1.00 (1) |
| Gly | 1.05 (1) |
| Nva | 1.10 (1) |
| Cha | 1.09 (1) |
| Pro | 1.04 (1) |

HPLC analysis spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 38.1 minutes.
FAB-MS: M+H Calculated 627.3, Found 627

[Example 25]

Synthesis of Pro-Ser-Phe-Gly-Asp-Trp-OH (SEQ ID NO:38)

The titled peptide was synthesized by the same procedure as in Example 1.

| Amino acid analysis (6N HCl + phenol, 24 hr, 110° C.) | |
|---|---|
| Asp | 0.99 (1) |
| Ser | 1.00 (1) |
| Gly | 1.02 (1) |
| Phe | 1.01 (1) |
| Trp | — (1) |
| Pro | 1.06 (1) |

HPLC analysis spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 38.3 minutes.
FAB-MS: M+H Calculated 709.3, Found 709

[Example 26]

Synthesis of Pro-Ser-Phg-Gly-Asp-Trp-OH (SEQ ID NO:35)

The titled peptide was synthesized by the same procedure as in Example 1.

| Amino acid analysis (6N HCl + phenol, 24 hr, 110° C.) | |
|---|---|
| Asp | 1.03 (1) |
| Ser | 1.00 (1) |
| Gly | 1.09 (1) |
| Phg | 1.10 (1) |
| Trp | — (1) |
| Pro | 1.08 (1) |

HPLC analysis

A spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 36.1 minutes.
FAB-MS: M+H Calculated 695.3, Found 695

[Example 27]

Synthesis of Pro-Ser-Hyp-Gly-Asp-Trp-OH (SEQ ID NO:39)

The titled peptide was synthesized by the same procedure as in Example 1.

| Amino acid analysis (6N HCl + phenol, 24 hr, 110° C.) | |
|---|---|
| Asp | 0.96 (1) |
| Ser | 1.00 (1) |
| Gly | 1.10 (1) |
| Hyp | 1.04 (1) |
| Trp | — (1) |
| Pro | 1.11 (1) |

HPLC analysis

A spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 19.7 minutes.
FAB-MS: M+H Calculated 674.3, Found 674

[Example 28]

Synthesis of Pro-Ser-DPro-Gly-Asp-Trp-OH (SEQ ID NO:60)

The titled peptide was synthesized by the same procedure as in Example 1.

| Amino acid analysis (6N HCl + phenol, 24 hr, 110° C.) | |
|---|---|
| Asp | 0.99 (1) |
| Ser | 1.00 (1) |
| Gly | 1.13 (1) |
| Trp | — (1) |
| Pro | 2.05 (2) |

HPLC analysis spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 21.0 minutes.
FAB-MS: M+H Calculated 658.3, Found 658

[Example 29]

Synthesis of Pro-Ser-Azt-Gly-Asp-Trp-OH (SEQ ID NO:58)

The titled peptide was synthesized by the same procedure as in Example 1.

| Amino acid analysis (6N HCl + phenol, 24 hr, 110° C.) | |
|---|---|
| Asp | 1.10 (1) |
| Ser | 1.03 (1) |
| Gly | 1.15 (1) |
| Trp | — (1) |
| Pro | 1.08 (1) |

HPLC analysis

A spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 20.5 minutes.

FAB-MS: M+H Calculated 644.3, Found 644

[Example 30]

Synthesis of Pro-Ser-Thz-Gly-Asp-Trp-OH (SEQ ID NO:55)

The titled peptide was synthesized by the same procedure as in Example 1.

| Amino acid analysis (6N HCl + phenol, 24 hr, 110° C.) | |
|---|---|
| Asp | 0.98 (1) |
| Ser | 1.00 (1) |
| Gly | 1.06 (1) |
| Trp | — (1) |
| Pro | 1.08 (1) |

HPLC analysis

A spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 23.5 minutes.

FAB-MS: M+H Calculated 676.3, Found 676

[Example 31]

Synthesis of Pro-Ser-Dmt-Gly-Asp-Trp-OH (SEQ ID NO:56)

The titled peptide was synthesized by the same procedure as in Example 1.

| Amino acid analysis (6N HCl + phenol, 24 hr, 110° C.) | |
|---|---|
| Asp | 1.05 (1) |
| Ser | 1.02 (1) |
| Gly | 1.10 (1) |
| Trp | — (1) |
| Pro | 1.07 (1) |

HPLC analysis spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 30.1 minutes.

FAB-MS: M+H Calculated 704.3, Found 704

[Example 32]

Synthesis of Pro-Ser-ΔA Pro-Gly-Asp-Trp-OH (SEQ ID NO:49)

The titled peptide was synthesized by the same procedure as in Example 1.

| Amino acid analysis (6N HCl + phenol, 24 hr, 110° C.) | |
|---|---|
| Asp | 0.99 (1) |
| Ser | 1.00 (1) |
| Gly | 1.00 (1) |
| Trp | — (1) |
| Δ Pro | 1.10 (1) |
| Pro | 1.08 (1) |

HPLC analysis spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 22.1 minutes.

FAB-MS: M+H Calculated 657.3, Found 657

[Example 33]

Synthesis of Pro-Ser-Hyp(Bzl)-Gly-Asp-Trp-OH (SEQ ID NO:59)

The titled peptide was synthesized by the same procedure as in Example 1.

| Amino acid analysis (6N HCl + phenol, 24 hr, 110° C.) | |
|---|---|
| Asp | 1.05 (1) |
| Ser | 1.02 (1) |
| Gly | 1.10 (1) |
| Trp | — (1) |
| Pro | 1.10 (1) |

HPLC analysis

A spectrum of analytical HPLC using Cosmosil 5C18-AR (φ4.6×200 mm) column at a flow rate of 1.0 ml/min by elution in a gradient of acetonitrile of 10–40% (60 min) in 0.1% TFA indicated a single peak at a retention time of 38.2 minutes.

FAB-MS: M+H Calculated 764.3, Found 764 [Experimental Example 1]Platelet Aggregation-Inhibiting Ability of the Compounds of the Present Invention Measurement of Activity in the Synthetic Peptide

[Measurement of in Vitro Human Platelet Aggregation using PRP]

Healthy male volunteers who had not taken any medicines for at least two weeks were treated as subjects. Blood was collected from the forearm vein of each subject on an empty stomach using a plastic syringe in which 1/10 volume of a 3.8% sodium citrate solution had been preliminarily charged and which was equipped with a #19 needle. Immediately after the blood collection, the syringe was stirred gently to mix the blood with the sodium citrate solution. The mixed blood was centrifuged (1100 rpm, 250 g) at room temperature for 15 minutes and the rotation was stopped without applying the brake. Then, the supernatant was collected with a Komagome type pipette to obtain platelet-rich plasma (PRP). The PRP was stored at room temperature. The blood remaining after centrifuging was further centrifuged (3500 rpm, 1500 g) at room temperature for 15 minutes and the rotation was stopped without applying the brake. The supernatant was collected to obtain platelet-poor plasma (PPP). After the preparation of the PRP, the number of platelets was counted and samples containing more than $2\times10^8$/ml of platelets were used for the following experiments.

Platelet aggregation was measured using an 8-channel platelet aggregation measuring instrument (Hematracer, Nikoh Bioscience, Tokyo, Japan) on the basis of the change in light transmittance through PRP. First, PPP and PRP (each 200 μl) were placed in glass cuvettes and incubated at 37° C. Thereafter, the transmittance was measured. The transmittance of PPP was determined as 100% and that of PRP as 0%. Then, 10 μl of saline or a sample-containing saline was added to PRP and incubated at 37° C. for one minute. A collagen solution (10 μl) at a concentration of 100μg/ml was added (final concentration: 5μg/ml) to induce aggregation and thereafter the transmittance was measured over 7 min-present invention having the base skeleton that had the Pro-Set struture at the N-terminus and into which guanidino group-free amino acids were introduced exhibited greatly increased platelet aggregation-inhibiting activity compared to the amino acid sequence RGDS (SEQ ID NO:70)which was present in the fibrinogen molecule (Table 2, Comparative Example 2).

TABLE 2

Platelet Aggregation-Inhibiting Activity of the Peptides of the Present Invention

| Peptide | | | $IC_{50}$ |
|---|---|---|---|
| Pro—Ser—Ala—Sar—Asp—Trp—OH | (SEQ ID NO: 8) | (Example 1) | $2.2 \times 10^{-6}$ M |
| Pro—Ser—Ala—Gly—Asp—Trp—OH | (SEQ ID NO: 7) | (Example 2) | $4.6 \times 10^{-6}$ M |
| Pro—Ser—Val—Sar—Asp—Trp—OH | (SEQ ID NO: 25) | (Example 3) | $7.3 \times 10^{-6}$ M |
| Pro—Ser—Nva—Gly—Asp—Trp—OH | (SEQ ID NO: 1) | (Example 4) | $5.4 \times 10^{-7}$ M |
| Pro—Ser—Nva—Sar—Asp—Trp—OH | (SEQ ID NO: 2) | (Example 5) | $1.4 \times 10^{-6}$ M |
| Pro—Ser—Leu—Gly—Asp—Trp—OH | (SEQ ID NO: 27) | (Example 6) | $1.3 \times 10^{-6}$ M |
| Pro—Ser—Leu—Sar—Asp—Trp—OH | (SEQ ID NO: 28) | (Example 7) | $2.0 \times 10^{-6}$ M |
| Pro—Ser—Nle—Sar—Asp—Trp—OH | (SEQ ID NO: 5) | (Example 8) | $5.2 \times 10^{-5}$ M |
| Pro—Ser—Nle—Gly—Asp—Trp—OH | (SEQ ID NO: 4) | (Example 9) | $8.4 \times 10^{-7}$ M |
| Pro—Ser—Ala—Sar—Asp—Phe—OH | (SEQ ID NO: 10) | (Example 10) | $4.1 \times 10^{-6}$ M |
| Pro—Ser—Gly—Sar—Asp—Trp—OH | (SEQ ID NO: 12) | (Example 11) | $3.7 \times 10^{-6}$ M |
| Pro—Ser—Ile—Sar—Asp—Trp—OH | (SEQ ID NO: 32) | (Example 12) | $5.0 \times 10^{-6}$ M |
| Pro—Ser—Lys—Gly—Asp—Trp—OH | (SEQ ID NO: 61) | (Example 13) | $1.4 \times 10^{-6}$ M |
| Pro—Ser—Ile—Gly—Asp—Trp—OH | (SEQ ID NO: 31) | (Example 14) | $1.0 \times 10^{-6}$ M |
| Pro—Ser—Ser—Gly—Asp—Trp—OH | (SEQ ID NO: 43) | (Example 15) | $5.0 \times 10^{-6}$ M |
| Pro—Ser—Nva—Gly—Asp—Phe—OH | (SEQ ID NO: 62) | (Example 16) | $1.0 \times 10^{-5}$ M |
| Pro—Ser—Nva—Gly—Asp—Hph—OH | (SEQ ID NO: 63) | (Example 17) | $1.1 \times 10^{-5}$ M |
| Pro—Ser—Nva—Gly—Asp—Tyr(CH$_3$)—OH | (SEQ ID NO: 64) | (Example 18) | $3.4 \times 10^{-6}$ M |
| Pro—Ser—Pro—Gly—Asp—Trp—OH | (SEQ ID NO: 40) | (Example 19) | $6.0 \times 10^{-7}$ M |
| Pro—Ser-(allo)Ile—Gly—Asp—Trp—OH | (SEQ ID NO: 34) | (Example 20) | $1.0 \times 10^{-6}$ M |
| Pro—Ser—Tle—Gly—Asp—Trp—OH | (SEQ ID NO: 19) | (Example 21) | $7.0 \times 10^{-7}$ M |
| Pro—Ser—Chg—Gly—Asp—Trp—OH | (SEQ ID NO: 36) | (Example 22) | $6.0 \times 10^{-7}$ M |
| Pro—Ser—Met—Gly—Asp—Trp—OH | (SEQ ID NO: 14) | (Example 23) | $2.0 \times 10^{-6}$ M |
| Pro—Ser—Nva—Gly—Asp—Cha—OH | (SEQ ID NO: 65) | (Example 24) | $4.0 \times 10^{-6}$ M |
| Pro—Ser—Phe—Gly—Asp—Trp—OH | (SEQ ID NO: 38) | (Example 25) | $1.0 \times 10^{-6}$ M |
| Pro—Ser—Phg—Gly—Asp—Trp—OH | (SEQ ID NO: 35) | (Example 26) | $1.0 \times 10^{-6}$ M |
| Pro—Ser—Hyp—Gly—Asp—Trp—OH | (SEQ ID NO: 39) | (Example 27) | $6.0 \times 10^{-7}$ M |
| Pro—Ser—DPro—Gly—Asp—Trp—OH | (SEQ ID NO: 60) | (Example 28) | $6.0 \times 10^{-7}$ M |
| Pro—Ser—Azt—Gly—Asp—Trp—OH | (SEQ ID NO: 58) | (Example 29) | $5.1 \times 10^{-6}$ M |
| Pro—Ser—Thz—Gly—Asp—Trp—OH | (SEQ ID NO: 55) | (Example 30) | $5.0 \times 10^{-7}$ M |
| Pro—Ser—Dmt—Gly—Asp—Trp—OH | (SEQ ID NO: 56) | (Example 31) | $5.0 \times 10^{-7}$ M |
| Pro—Ser-Δ Pro—Gly—Asp—Trp—OH | (SEQ ID NO: 49) | (Example 32) | $3.0 \times 10^{-7}$ M |
| Pro—Ser—Hyp(Bzl)—Gly—Asp—Trp—OH | (SEQ ID NO: 59) | (Example 33) | $5.0 \times 10^{-7}$ M |
| Pro—Ser—Orn—Gly—Asp—Trp—OH | (SEQ ID NO: 66) | (Comparative Example 1) | $6.3 \times 10^{-4}$ M |
| Arg—Gly—Asp—Ser—OH | (SEQ ID NO: 67) | (Comparative Example 2) | $4.6 \times 10^{-4}$ M | utes. The experiment was carried out using those samples in which aggregation with collagen and ADP was confirmed in the first step and in which the maximum rate of the aggregation with collagen was at least 70%.

The sample was dissolved in saline at a concentration of $2.2 \times 10^{-2}$M and a 2-fold dilution series was prepared for use in the experiments. The samples insoluble in saline were dissolved in saline containing 10% Dimethyl sulfoxide.

The results were calculated as follows:

$$\begin{matrix} \text{Percent} \\ \text{aggrega-} \\ \text{tion} \\ \text{inhibition} \end{matrix} = \left[ 1 - \frac{\text{Maximum percent aggregation when the sample is added}}{\text{Maximum percent aggregation when saline is added}} \right] \times 100 \quad \begin{matrix} \text{Calculation} \\ \text{Formula (1)} \end{matrix}$$

A graph was constructed by plotting the percent aggregation inhibition against sample concentration and from the graph, the concentration at which the aggregation was inhibited by 50% ($IC_{50}$) was calculated. $IC_{50}$ of each sample is shown in Table 2. Table 2 shows that the peptides of the It was verified that the platelet aggregation-inhibiting ability of the peptides of the present invention is remarkably improved compared to that of the amino acid sequence RGDS-OH (SEQ ID NO:72) (purchased from Peptide Laboratory, Minoo-shi, Japan) that is listed as Comparative Example 2 in Table 2 and which is contained in the fibrinogen molecule.

[Experimental Example 2]Acute Toxicity Test

The peptide obtained in Example 1 was intravenously injected into a mouse in an amount of 100 mg/Kg but no toxicity was observed.

[Experimental Example 3]Application of the peptides of the present invention to blood coagulation-inhibiting agents for extracorporeal circulation.

In order to confirm that the peptides of the present invention have action of inhibiting blood coagulation in extracorporeal circulation systems, such as hemodialysis of artificial lung, experiments were carried out on an artificial hemodialysis model using a beagle according to the method described elsewhere (see Hamano et al., Thromb. Res. 55 (1989) pp.438-449) with some modifications. A scheme of the dialysis circuit in a dog hemodialysis model is shown in FIG. 1.

In the experiments, beagles (either male or female) weighing 10-12 kg were used. The beagles were anesthetized with pentobarbital (about 30 mg/kg) and the right hind legs were incised to expose the femoral artery and femoral vein. Cannulas with silicon tubes were inserted into the femoral artery and femoral vein and these silicon tubes were connected to a hollow-fiber dialyzer (RENAK-A, RA-04, 0.4 $m^2$, Kawasumi Lab. Tokyo). During this operation, no anti-coagulants such as heparin were used. A blood perfusion pump was placed between the femoral artery and the dialyzer and operated to keep the blood flow rate at 25 ml/min in the extracorporeal circulation system during the experiments. Dialysate was not circulated and after the hydrostatic pressure of about 100 cm $H_2O$ was applied to the outer space of the hollow fibers of the dialyzer, the inlet and outlet for dialysate circuit were sealed.

The following three parameters were measured in the experiments; (1) the pressure at the proximal portion of the dialyzer (perfusion pressure), (2) the extent of platelet adhesion (which is a parameter of platelet function and the extent of platelet activation) and (3) the whole blood coagulation time (the parameter of the extent of activation of blood coagulation system). The perfusion pressure was measured by a pressure gauge incorporated in the proximal portion of the dialyzer as shown in FIG. 1. Since at the site of dialyzer, blood often experiences contacts with foreign materials and blood flows in a narrow space, blood coagulation is most likely to occur at this site in the dialysis circuit. If blood coagulation occurs there, the dialyzer is clogged and the blood pressure at the proximal portion will increase. The change in the perfusion pressure at this site indicates the degree of blood coagulation in the dialysis circuit. An aliquot of blood was sampled at the inlet and outlet of the dialysis part at given intervals to measure the parameters (2) and (3), which were measured by conventional methods.

Immediately after the circuit set-up, blood was circulated through the circuit and an injection of a saline solution of the peptide of the present invention was begun from the arterial side. The total amount of the injection was 10 mg/dog and this was gradually administered over 1 hour (injection rate; 1 ml/min). In a control experiment, only saline was continuously injected in the same manner. The injection of the drug was stopped after 60 minutes and blood was thereafter circulated up to 180 minutes to continue the measurement of the above parameters. When the perfusion pressure exceeded 500 mmHg, the experiment was stopped at that time.

Figure 2:
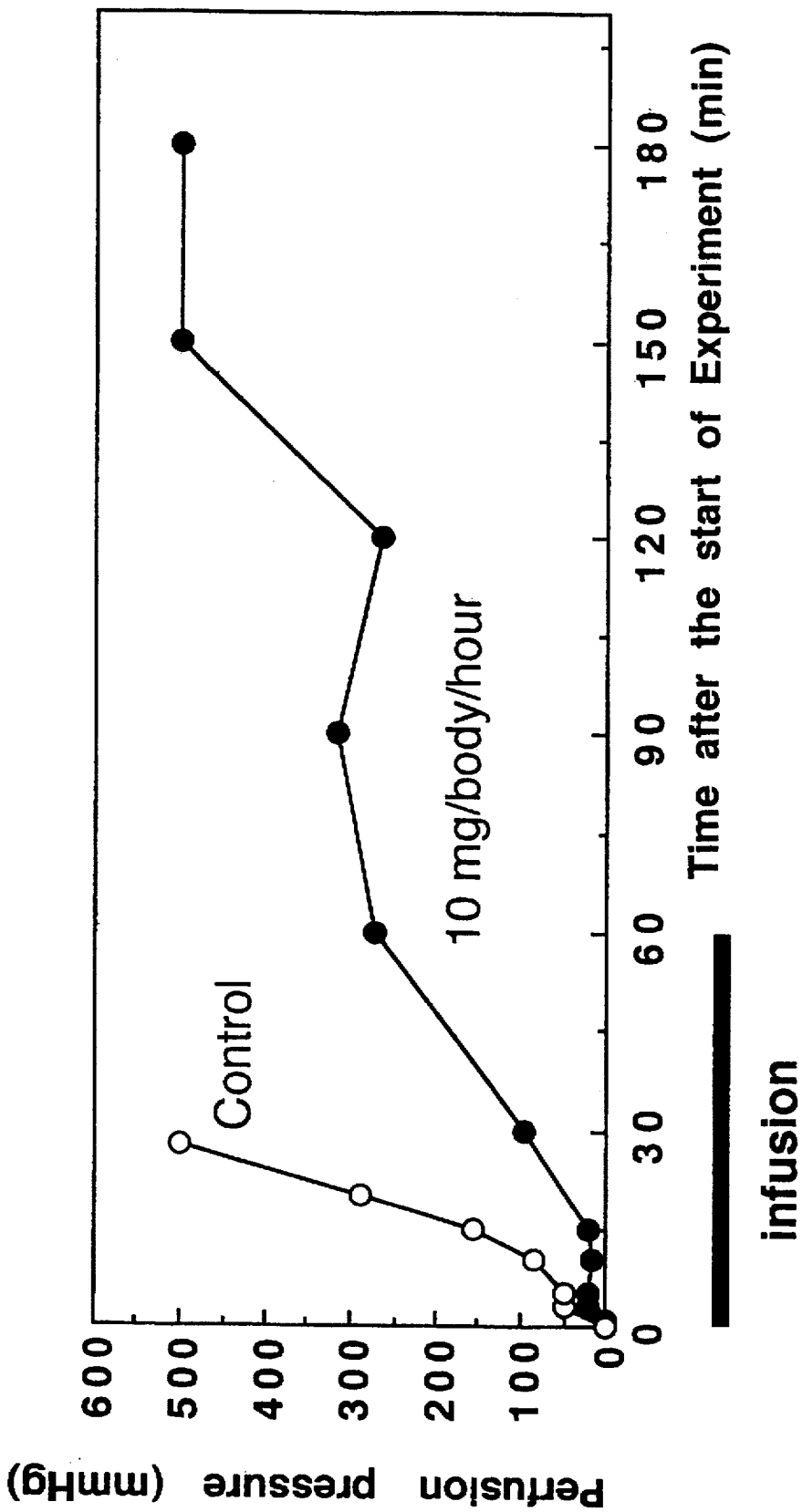
FIG. 2 is a graph showing blood coagulation-inhibiting effect in a dog hemodialysis model.

FIG. 2 shows the results of the experiments in which the inhibitory effect of the compound of Example 19 on the increase in the perfusion pressure was examined. The numbers on the abscissa indicate the time after the beginning of the drug infusion and those on the ordinate indicate the perfusion pressure. The perfusion pressure was 0-30 mmHg right after the start of the blood flow and increased due to the occurrence of the blood coagulation. In the control group in which no anti-coagulant was injected, the perfusion pressure increased rapidly after 10 minutes and exceeded 500 mmHg in 25 minutes, making further measurements impossible. As shown in this case, without anti-coagulants blood coagulation occurred rapidly in the dialysis circuit, particularly at the site of the dialyzer. In contrast, when the peptide of the present invention prepared in Example 19 was injected, blood coagulation was obviously inhibited.

With respect to the platelet adhesion ability and the whole blood coagulation time, changes almost parallel to the increase pattern of the perfusion pressure were observed. Briefly, in the control group, the increase in the platelet adhesion ability and the decrease in the whole blood coagulation time were observed with the passage of time. This indicates that platelets were activated and thereby the blood coagulation system was activated and that as a result, the dog was under such conditions that blood coagulation was highly likely to occur. In contrast, in the group into which the peptide of the present invention was injected, it was revealed that the blood coagulation ability dropped to approximately 0% during the continuous injection of the drug and that, therefore, the dog was under such conditions that platelet activation was completely inhibited. In addition, the whole blood coagulation time was significantly prolonged during this period.

As shown above, the peptides of the present invention inhibited completely the blood coagulation in an extracorporeal circulation system. This indicates that the peptides of the present invention can satisfactorily be used as a substitute for currently used anti-coagulant heparin. As described above, although heparin completely inhibits blood coagulation in an extracorporeal system, it has the disadvantage that it is only slightly eliminated from the body and thereby inhibits blood coagulation while promoting hemorrhagic tendency for several hours even after the hemodialysis. In contrast, the peptides of the present invention are highly degradable in the body (cleared within about 30 min from the body). Therefore it is thought that the peptides of the present invention are superior to heparin or its relevant drugs in that blood coagulation activity will return to normal level soon after the stoppage of the drug administration. Furthermore, since the peptides of the present invention are extremely low in toxicity, they are promising as new blood coagulation-inhibiting agents that compensate for the disadvantages of heparin.

As shown above, if the peptides of the present invention are dissolved in saline or sodium citrate solution and if they are injected continuously at a rate of approximately 1-3 mg/hour/kg from the inlet of the extracorporeal circulation system by means of drop infusion and the like, satisfactory blood coagulation-inhibiting action can be expected. If is believed that in the actual application to humans, the dose can be further reduced.

If the peptides of the present invention are combined with other anti-coagulants with entirely different modes of action such as a sodium citrate solution, heparin, futhan, fibrinolytic agents and the like, synergistic effect can be expected. Therefore, the dose of both drugs can be reduced and greater safety is insured.

[Experimental Example 4]Applicability of the Peptides of the Present Invention to Agents for Protecting Platelet Preparations for Blood Transfusion Hartley guinea pigs (male; body weight 350-400 g) were used in this experiment. After the guinea pigs were anesthetized with ether, the peritoneal cavities were opened and blood was collected from the peritoneal artery. The blood collection was performed using a syringe in which a preliminarily sterilized 3.8% sodium citrate solution had been charged in a 1/10 volume and which was equipped with a #24 needle. Immediately after the blood collection, the syringe was stirred gently to mix the blood with the sodium citrate solution. The mixed blood was centrifuged (900 rpm) at room temperature for 15 minutes and the rotation was stopped. Then, the supernatant was collected with a Komagome-type pipette aseptically to give a platelet fraction for storage.

After the platelet fraction was transferred into a platelet storage bag (TERUMO CORP., Separation Bag S for Apheresis), the bag was placed on a shaker and preserved while shaking with a shaking amplitude of 20 cm and at a shaking frequency of 20 Hz at room temperature.

After storage for a given period of time, an aliquot of the platelet fraction was sampled and the number of platelets was measured. The storage fraction was adjusted at pH 6.5 with a citric acid solution and centrifuged (2000 rpm, 15 minutes) at room temperature. After the supernatant was removed, a Ca-Tyrode solution (pH 6.5) with apyrase (Sigma Co., final concentration 0.2 U/ml) was added to resuspend platelets. After being left to stand for 20 minutes at room temperature, the suspension was centrifuged (2000 rpm, 15 minutes) and the supernatant was removed. The suspension was washed again in the same manner and the platelets were resuspended in preliminarily preserved guinea pig plasma (the number of platelets; about $3 \times 10^8$/ml). The aggregation ability of the platelets was determined using this platelet suspension by the same method as in Experimental Example 1.

Figure 3:
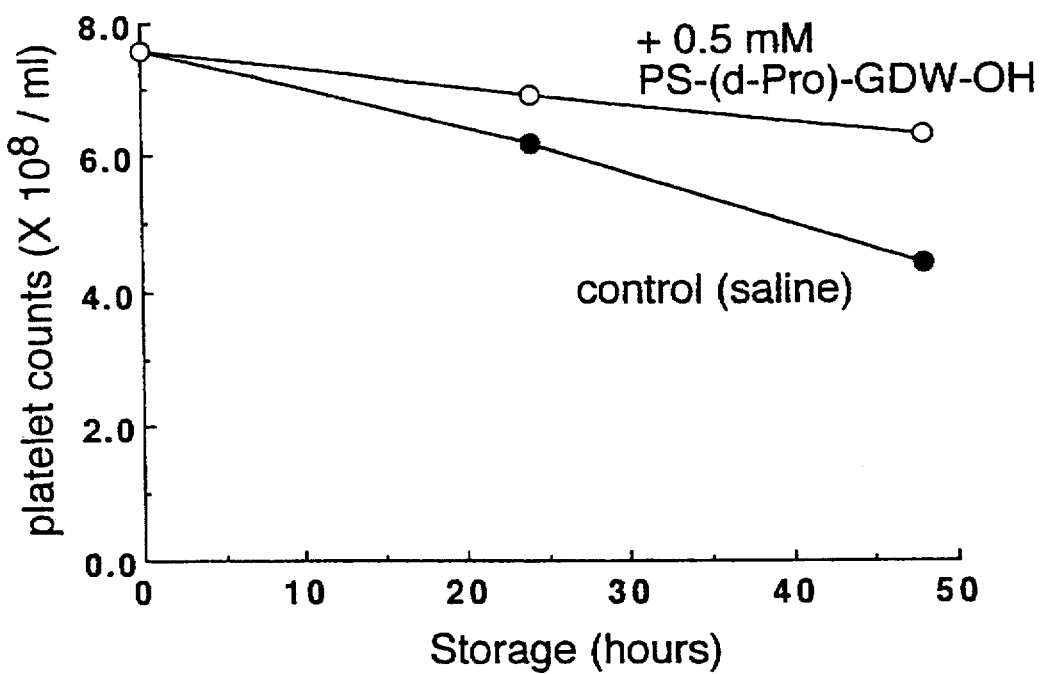
FIG. 3 is a graph showing the protective effect of the peptide of the present invention against the decrease in platelet counts during storage.

FIG. 3 shows the change in platelet count during the storage. In the control group to which only physiological saline was added, the platelet count decreased greatly during the storage. In contrast, in the group to which the compound prepared in Example 28 was added, a significant inhibitory effect on the decrease in platelet count was observed compared to the control group. This protective effect was dependent on the concentration of the peptide added, indicating that the peptide of the present invention itself has the protective action on platelets.

Figure 4:
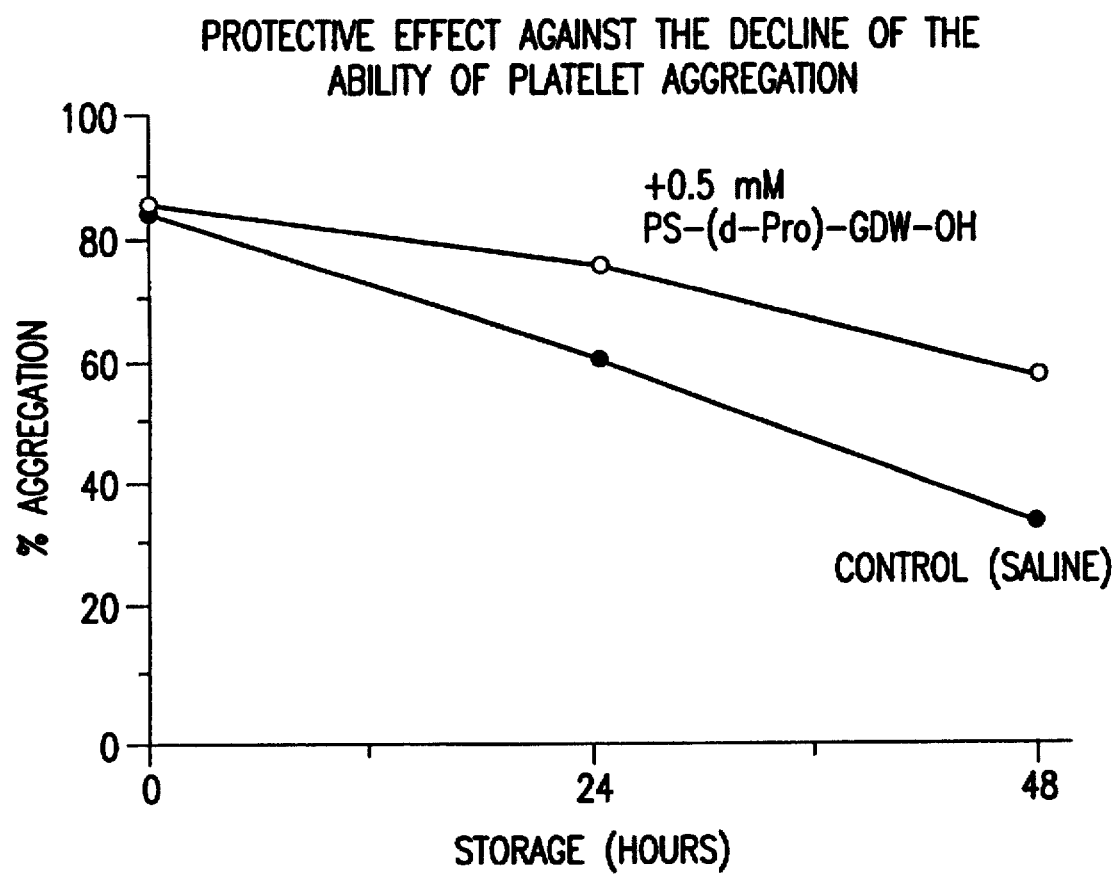
FIG. 4 is a graph showing the protective effect of the peptide of the present invention against the decline of the ability of platelet aggregation.

FIG. 4 shows the time-dependent change in the platelet aggregation ability during the storage. In the control group to which no drug was added, the aggregation activity of platelets declined to less than 40% after storage for 48 hours. In the group to which the compound prepared in Example 28 was added, at least 60% of the aggregation activity of platelets remained after the 48 hour storage. This indicates that the decline in the aggregation activity of the platelets was significantly inhibited by the addition of the compound.

As shown above, the addition of the peptide of the present invention produced platelet-protective effects during storage such as the inhibition of the decrease in platelet count, platelet aggregation ability, and the like. It has already been confirmed that even if the peptide compounds heretofore in use such as RGDS (SEQ ID NO:70), RGDF (SEQ ID NO:68) and the like are added to platelet fractions, they are broken down by the action of enzymes present in plasma and hence are clearly unsuitable for use in long-term storage of platelets. On the other hand, compounds that are very stable and which will not be easily broken down in the body will inhibit all the functions of platelets in the body after blood transfusion and thereby lower the efficiency of transfusion. In contrast, the peptides of the present invention have desirable features such as high stability in platelet fractions, high in vivo degradability and low toxicity and, therefore, they are believed to be useful as excellent platelet protecting agents.

In addition, if the peptides of the present invention are administered as acetate salt or phosphate salt, they are expected to manifest a buffering action and thereby produce inhibitory effects against the change of pH during the storage of platelet fractions. Moreover, if the peptides of the present invention are not used alone but are combined with aspirin or other platelet aggregation-inhibiting agents having different modes of action, synergistic effects can be expected.

[Formulation Example 1]

Each of the peptides obtained in Examples 1-31 (100 mg) was dissolved in 100 ml of saline. Under aseptic conditions, the obtained solution was charged in a 2.5 ml volume ampule and the ampule was sealed to prepare an injection preparation.

[Formulation Example 2]

A mixture (1 ml) of ethanol and water was added to a mixture consisting of one of the peptides obtained in Examples 1-31 (500 mg), crystalline cellulose (50 mg) and lactose (450 mg) and blended intimately. The obtained mixture was granulated by a conventional method to prepare granules.

INDUSTRIAL APPLICABILITY

As explained above, the peptides of the present invention are useful as platelet aggregation-inhibiting agents. In other words, the peptides of the present invention are useful for preventing thrombolus, thromboembolism and reobstruction during and after the treatment of thrombolysis, preventing thrombolus, thromboembolism and reobstruction after angioplasty of coronary arteries and other arteries and after coronary artery bypassing, and preventing cardiac infarction.

In addition, the peptides of the present invention are useful as blood coagulation-inhibiting agents for extracorporeal circulation for inhibiting thrombus formation at the time of extracorporeal circulation.

Furthermore, the peptides of the present invention are effective in suppressing the decrease in the function of platelets, that is, they are effective in protecting platelets. Moreover, the peptides of the present invention are effective as cell adhesion-inhibiting agents in inhibiting tumor metastasis.

What is claimed:

1. A peptide or a salt thereof, that is represented by the following general formula (I):

Pro-Ser-A-B-Asp-C-D (SEQ ID NO:71)   (I)

wherein A is an amino acid other than amino acids having a guanidino group at a side chain, B is an amino acid selected from the group consisting of glycine, alanine, βalanine and N-alkyl substitution products thereof, C is an amino acid having a hydrophobic group as a side chain and D is a hydroxy or an amino group.

2. The peptide or salt thereof according to claim 1, wherein A is a neutral amino acid.

3. The peptide or salt thereof according to claim 2, wherein said neutral amino acid is glycine, proline, a $C_1$–$C_{10}$N-alkyglycine, a proline derivative having a substituent on the pyrrolidine ring, a proline derivative having an unsaturated bond or a heteroatom in the pyrrolidine ring, or a proline derivative having 4 to 8 membered ring.

4. The peptide or salt thereof according to claim 2, wherein said neutral amino acid is an amino acid having as a side chain at least one group selected from the class consisting of substituted or unsubstituted alkyl having 1–30 carbon atoms, substituted or unsubstituted aryl, substituted or unsubstituted heteroaryl, and substituted or unsubstituted cycloalkyl having 3–10 carbon atoms.

5. The peptide or salt thereof according to claim 1, wherein A is an amino acid having as a side chain an amino group that may be substituted with an alkyl group having 1–10 carbon atoms.

6. The peptide or salt thereof according to claim 1, wherein A is an amino acid represented by the following general formula (X):

wherein, $R^1$ and $R^2$ which may be the same or different are each a hydrogen atom or an alkyl group having 1–10 carbon atoms, and n is an integer of 4–10.

7. The peptide or salt thereof according to claim 1, wherein B is glycine or an N-alkyl glycine.

8. The peptide or salt thereof according to claim 1, wherein C is tryptophan or phenylalanine.

9. The peptide or salt thereof according to claim 1, wherein A is a neutral amino acid or an amino acid having as a side chain an amino group that may be substituted with an alkyl group having 1–10 carbon atoms, B is glycine or an N-alkyl glycine, and C is tryptophan or phenylalanine.

10. A platelet aggregation-inhibiting agent comprising the compound or salt thereof according to claim 1 as an active ingredient.

11. A blood coagulation-inhibiting agent for extracorporeal circulation, comprising the compound or salt thereof according to claim 1 as an active ingredient.

12. A cell adhesion-inhibiting agent comprising the compound or salt thereof according to claim 1 as an active ingredient.

13. A tumor metastasis-inhibiting agent comprising the compound or salt thereof according to claim 1 as an active ingredient.

14. An agent for protecting platelet preparations for blood transfusion, comprising the compound or salt thereof according to claim 1 as an active ingredient.

15. A platelet preparation for blood transfusion, in which the compound or salt thereof according to claim 1 is added.

16. A platelet preparation pack for blood transfusion, comprising the compound or salt thereof according to claim 1 in a platelet preparation for blood transfusion in the pack.

17. A pharmaceutical composition comprising the compound or salt thereof according to claim 1 and a pharmaceutically acceptable carrier.

18. The pharmaceutical composition according to claim 17, which is used for inhibiting platelet aggregation.

19. The pharmaceutical composition according to claim 17, which is used for inhibiting the coagulation of blood for extracorporeal circulation.

20. The pharmaceutical composition according to claim 17, which is used for inhibiting cell adhesion.

21. The pharmaceutical composition according to claim 17, which is used for inhibiting tumor metastasis.

22. The pharmaceutical composition according to claim 17, which is used for protecting platelets for blood transfusion.

23. A method for inhibiting platelet aggregation, comprising the step of administering to a patient an effective amount of the compound or salt thereof according to claim 1 in a pharmaceutically acceptable carrier.

24. A method for inhibiting the coagulation of blood for extracorporeal circulation, comprising the step of administering to a patient an effective amount of the compound or salt thereof according to claim 1 in a pharmaceutically acceptable carrier.

25. A method for inhibiting cell adhesion, comprising the step of administering to a patient an effective amount of the compound or salt thereof according to claim 1 in a pharmaceutically acceptable carrier.

26. A method for inhibiting tumor metastasis, comprising the step of administering to a patient an effective amount of the compound or salt thereof according to claim 1 in a pharmaceutically acceptable carrier.

27. A method for protecting platelets in platelet preparation for blood transfusion, comprising the step of adding an effective amount of the compound or salt thereof according to claim 1 to the platelet preparation.

* * * * *

UNITED STATES PATENT AND TRADEMARK OFFICE
CERTIFICATE OF CORRECTION

PATENT NO. : 5,721,213
DATED : February 24, 1998
INVENTOR(S) : Yoshimi Sato, et al.

It is certified that error appears in the above-identified patent and that said Letters Patent is hereby corrected as shown below:

| Column | Line | |
|---|---|---|
| 5 | 1 | Change "Pro-Set" to --Pro-Ser--. |
| 5 | 16 | Change "gpllblla" to --gpIIbIIIa--. |
| 7 | 60 | Change "0-methyl" to --O-methyl--. |
| 8 | 46 | Change "Pro-Ser-ΔA" to --Pro-Ser-Δ--. |
| 8 | 60 | Change "Pro-Ser-ΔA" to --Pro-Ser-Δ--. |
| 8 | 62 | Change "Pro-Ser-ΔA" to --Pro-Ser-Δ--. |
| 10 | 66 | Change "$Bu^1$" to --$Bu^t$--. |
| 12 | 16 | Change "+30°" to -- -30° --. |
| 15 | 19 | Change "εbondasphere" to --μbondasphere-- |
| 19 | 11 | Change "spectrum" to --A spectrum--. |
| 19 | 34 | Change "spectrum" to --A spectrum--. |
| 19 | 56 | Change "spectrum" to --A spectrum--. |

UNITED STATES PATENT AND TRADEMARK OFFICE
CERTIFICATE OF CORRECTION

PATENT NO. : 5,721,213
DATED : February 24, 1998
INVENTOR(S) : Yoshimi Sato, et al.

It is certified that error appears in the above-identified patent and that said Letters Patent is hereby corrected as shown below:

| Column | Line | |
|---|---|---|
| 20 | 11 | Change "spectrum" to --A spectrum--. |
| 20 | 56 | Change "spectrum" to --A spectrum--. |
| 21 | 11 | Change "spectrum" to --A spectrum--. |
| 21 | 34 | Change "spectrum" to --A spectrum--. |
| 21 | 56 | Change "spectrum" to --A spectrum--. |
| 22 | 34 | Change "spectrum" to --A spectrum--. |
| 22 | 56 | Change "spectrum" to --A spectrum--. |
| 23 | 11 | Change "spectrum" to --A spectrum--. |
| 23 | 34 | Change "spectrum" to --A spectrum--. |
| 23 | 56 | Change "spectrum" to --A spectrum--. |
| 24 | 56 | Change "spectrum" to --A spectrum--. |
| 25 | 56 | Change "spectrum" to --A spectrum--. |
| 26 | 12 | Change "spectrum" to --A spectrum--. |

UNITED STATES PATENT AND TRADEMARK OFFICE
CERTIFICATE OF CORRECTION

PATENT NO.  : 5,721,213
DATED       : February 24, 1998
INVENTOR(S) : Yoshimi Sato, et al.

It is certified that error appears in the above-identified patent and that said Letters Patent is hereby corrected as shown below:

| Column | Line | |
|---|---|---|
| 28 | 2 | Change "Pro-Set" to --Pro-Ser--. |
| 57 | | Under "SEQ ID NO:56: (ix) FEATURE: (D)" change "thioproli" to --thioproline--. |
| 65 | 7 | Change "βalanine" to --β-alanine--. |

Signed and Sealed this

Sixth Day of October, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 71

( 2 ) INFORMATION FOR SEQ ID NO:1:

( i ) SEQUENCE CHARACTERISTICS:
      ( A ) LENGTH: 6 amino acids (B) TYPE: amino acid
(D) TOPOLOGY: linear (ii) MOLECULE TYPE: peptide (ix) FEATURE:
(B) LOCATION: amino acid 3
(D) OTHER INFORMATION: Xaa at position 3 is norvaline (xi) SEQUENCE DESCRIPTION: SEQ ID NO:1:

Pro Ser Xaa Gly Asp Trp
              5

(2) INFORMATION FOR SEQ ID NO:2:

(i) SEQUENCE CHARACTERISTICS:
(A) LENGTH: 6 amino acids
(B) TYPE: amino acid
(D) TOPOLOGY: linear (ii) MOLECULE TYPE: peptide (ix) FEATURE:
(B) LOCATION: amino acid 3
(D) OTHER INFORMATION: Xaa at position 3 is norvaline
(B) LOCATION: amino acid 4
(D) OTHER INFORMATION: Xaa at position 4 is sarcosine (xi) SEQUENCE DESCRIPTION: SEQ ID NO:2:

Pro Ser Xaa Xaa Asp Trp
              5

(2) INFORMATION FOR SEQ ID NO:3:

(i) SEQUENCE CHARACTERISTICS:
(A) LENGTH: 6 amino acids
(B) TYPE: amino acid
(D) TOPOLOGY: linear (ii) MOLECULE TYPE: peptide (ix) FEATURE:
(B) LOCATION: amino acid 3
(D) OTHER INFORMATION: Xaa at position 3 is norvaline (xi) SEQUENCE DESCRIPTION: SEQ ID NO:3:

Pro Ser Xaa Ala Asp Trp
              5

(2) INFORMATION FOR SEQ ID NO:4:

(i) SEQUENCE CHARACTERISTICS:
(A) LENGTH: 6 amino acids
(B) TYPE: amino acid
(D) TOPOLOGY: linear (ii) MOLECULE TYPE: peptide (ix) FEATURE:
(B) LOCATION: amino acid 3
(D) OTHER INFORMATION: Xaa at position 3 is norleucine (xi) SEQUENCE DESCRIPTION: SEQ ID NO:4:

Pro Ser Xaa Gly Asp Trp
              5

(2) INFORMATION FOR SEQ ID NO:5:

(i) SEQUENCE CHARACTERISTICS:
(A) LENGTH: 6 amino acids
(B) TYPE: amino acid
(D) TOPOLOGY: linear ( i i ) MOLECULE TYPE: peptide ( i x ) FEATURE:
    ( B ) LOCATION: amino acid 3
    ( D ) OTHER INFORMATION: Xaa at position 3 is norleucine
    ( B ) LOCATION: amino acid 4
    ( D ) OTHER INFORMATION: Xaa at position 4 is sarcosine ( x i ) SEQUENCE DESCRIPTION: SEQ ID NO:5:

Pro Ser Xaa Xaa Asp Trp
                      5

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( B ) LOCATION: amino acid 3
        ( D ) OTHER INFORMATION: Xaa at position 3 is norleucine ( x i ) SEQUENCE DESCRIPTION: SEQ ID NO:6:

Pro Ser Xaa Ala Asp Trp
                      5

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

Pro Ser Ala Gly Asp Trp
                      5

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( B ) LOCATION: amino acid 4
        ( D ) OTHER INFORMATION: Xaa at position 4 is sarcosine ( x i ) SEQUENCE DESCRIPTION: SEQ ID NO:8:

Pro Ser Ala Xaa Asp Trp
                      5

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

Pro Ser Ala Ala Asp Trp ( 2 ) INFORMATION FOR SEQ ID NO:10:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( B ) LOCATION: amino acid 4
        ( D ) OTHER INFORMATION: Xaa at position 4 is sarcosine ( x i ) SEQUENCE DESCRIPTION: SEQ ID NO:10:

Pro Ser Ala Xaa Asp Phe
                      5

( 2 ) INFORMATION FOR SEQ ID NO:11:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

Pro Ser Gly Gly Asp Trp
                      5

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( B ) LOCATION: amino acid 4
        ( D ) OTHER INFORMATION: Xaa at position 4 is sarcosine ( x i ) SEQUENCE DESCRIPTION: SEQ ID NO:12:

Pro Ser Gly Xaa Asp Trp
                      5

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

Pro Ser Gly Ala Asp Trp
                      5

( 2 ) INFORMATION FOR SEQ ID NO:14:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

Pro Ser Met Gly Asp Trp
                 5

( 2 ) INFORMATION FOR SEQ ID NO:15:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( B ) LOCATION: amino acid 5
    ( D ) OTHER INFORMATION: Xaa at position 5 is sarcosine ( x i ) SEQUENCE DESCRIPTION: SEQ ID NO:15:

Pro Ser Met Ala Xaa Trp
                 5

( 2 ) INFORMATION FOR SEQ ID NO:16:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:16:

Pro Ser Met Ala Asp Trp
                 5

( 2 ) INFORMATION FOR SEQ ID NO:17:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:17:

Pro Ser Cys Gly Asp Trp
                 5

( 2 ) INFORMATION FOR SEQ ID NO:18:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( B ) LOCATION: amino acid 3
    ( D ) OTHER INFORMATION: Xaa at position 3 is penicillamine ( x i ) SEQUENCE DESCRIPTION: SEQ ID NO:18:

Pro Ser Xaa Gly Asp Trp
                 5

( 2 ) INFORMATION FOR SEQ ID NO:19:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( B ) LOCATION: amino acid 3
    ( D ) OTHER INFORMATION: Xaa at position 3 is tertiary leucine ( x i ) SEQUENCE DESCRIPTION: SEQ ID NO:19:

Pro Ser Xaa Gly Asp Trp
                           5

( 2 ) INFORMATION FOR SEQ ID NO:20:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( B ) LOCATION: amino acid 3
        ( D ) OTHER INFORMATION: Xaa at position 3 is tertiary leucine
        ( B ) LOCATION: amino acid 4
        ( D ) OTHER INFORMATION: Xaa at position 4 is sarcosine ( x i ) SEQUENCE DESCRIPTION: SEQ ID NO:20:

Pro Ser Xaa Xaa Asp Trp
                           5

( 2 ) INFORMATION FOR SEQ ID NO:21:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( B ) LOCATION: amino acid 3
        ( D ) OTHER INFORMATION: Xaa at position 3 is tertiary leucine ( x i ) SEQUENCE DESCRIPTION: SEQ ID NO:21:

Pro Ser Xaa Ala Asp Trp
                           5

( 2 ) INFORMATION FOR SEQ ID NO:22:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( B ) LOCATION: amino acid 3
        ( D ) OTHER INFORMATION: Xaa at position 3 is tertiary leucine ( x i ) SEQUENCE DESCRIPTION: SEQ ID NO:22:

Pro Ser Xaa Gly Asp Phe
                           5

( 2 ) INFORMATION FOR SEQ ID NO:23:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
  ( B ) LOCATION: amino acid 3
  ( D ) OTHER INFORMATION: Xaa at position 3 is tertiary leucine
  ( B ) LOCATION: amino acid 4
  ( D ) OTHER INFORMATION: Xaa at position 4 is sarcosine ( x i ) SEQUENCE DESCRIPTION: SEQ ID NO:23:

Pro Ser Xaa Xaa Asp Phe
                  5

( 2 ) INFORMATION FOR SEQ ID NO:24:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:24:

Pro Ser Val Gly Asp Trp
                  5

( 2 ) INFORMATION FOR SEQ ID NO:25:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( B ) LOCATION: amino acid 4
    ( D ) OTHER INFORMATION: Xaa at position 4 is sarcosine ( x i ) SEQUENCE DESCRIPTION: SEQ ID NO:25:

Pro Ser Val Xaa Asp Trp
                  5

( 2 ) INFORMATION FOR SEQ ID NO:26:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:26:

Pro Ser Val Ala Asp Trp
                  5

( 2 ) INFORMATION FOR SEQ ID NO:27:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:27:

Pro Ser Leu Gly Asp Trp
                  5

( 2 ) INFORMATION FOR SEQ ID NO:28:

( i ) SEQUENCE CHARACTERISTICS:

( A ) LENGTH: 6 amino acids
( B ) TYPE: amino acid
( D ) TOPOLOGY: linear ( i i ) MOLECULE TYPE: peptide ( i x ) FEATURE:
( B ) LOCATION: amino acid 4
( D ) OTHER INFORMATION: Xaa at position 4 is sarcosine ( x i ) SEQUENCE DESCRIPTION: SEQ ID NO:28:

Pro  Ser  Leu  Xaa  Asp  Trp
                    5

( 2 ) INFORMATION FOR SEQ ID NO:29:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( i x ) FEATURE:

( x i ) SEQUENCE DESCRIPTION: SEQ ID NO:29:

Pro  Ser  Leu  Ala  Asp  Trp
                    5

( 2 ) INFORMATION FOR SEQ ID NO:30:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( x i ) SEQUENCE DESCRIPTION: SEQ ID NO:30:

Pro  Ser  Leu  Gly  Asp  Phe
                    5

( 2 ) INFORMATION FOR SEQ ID NO:31:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( x i ) SEQUENCE DESCRIPTION: SEQ ID NO:31:

Pro  Ser  Ile  Gly  Asp  Trp
                    5

( 2 ) INFORMATION FOR SEQ ID NO:32:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( i x ) FEATURE:
( B ) LOCATION: amino acid 4
( D ) OTHER INFORMATION: Xaa at position 4 is sarcosine ( x i ) SEQUENCE DESCRIPTION: SEQ ID NO:32:

Pro  Ser  Ile  Xaa  Asp  Trp
                    5

( 2 ) INFORMATION FOR SEQ ID NO:33:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:33:

Pro Ser Ile Ala Asp Trp
              5

( 2 ) INFORMATION FOR SEQ ID NO:34:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( i x ) FEATURE:
      ( B ) LOCATION: amino acid 3
      ( D ) OTHER INFORMATION: Xaa at position 3 is allo isoleucine ( x i ) SEQUENCE DESCRIPTION: SEQ ID NO:34:

Pro Ser Xaa Gly Asp Trp
              5

( 2 ) INFORMATION FOR SEQ ID NO:35:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( i x ) FEATURE:
      ( B ) LOCATION: amino acid 3
      ( D ) OTHER INFORMATION: Xaa at position 3 is phenylglycine ( x i ) SEQUENCE DESCRIPTION: SEQ ID NO:35:

Pro Ser Xaa Gly Asp Trp
              5

( 2 ) INFORMATION FOR SEQ ID NO:36:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( i x ) FEATURE:
      ( B ) LOCATION: amino acid 3
      ( D ) OTHER INFORMATION: Xaa at position 3 is cyclohexyl glycine ( x i ) SEQUENCE DESCRIPTION: SEQ ID NO:36:

Pro Ser Xaa Gly Asp Trp
              5

( 2 ) INFORMATION FOR SEQ ID NO:37:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( i x ) FEATURE:
  ( B ) LOCATION: amino acid 3
  ( D ) OTHER INFORMATION: Xaa at position 3 is cyclohexyl alanine ( x i ) SEQUENCE DESCRIPTION: SEQ ID NO:37:

Pro Ser Xaa Gly Asp Trp
            5

( 2 ) INFORMATION FOR SEQ ID NO:38:

( i ) SEQUENCE CHARACTERISTICS:
  ( A ) LENGTH: 6 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:38:

Pro Ser Phe Gly Asp Trp
            5

( 2 ) INFORMATION FOR SEQ ID NO:39:

( i ) SEQUENCE CHARACTERISTICS:
  ( A ) LENGTH: 6 amino acids
  ( B ) TYPE: amino acid
  ( D ) TOPOLOGY: linear ( i i ) MOLECULE TYPE: peptide ( i x ) FEATURE:
  ( B ) LOCATION: amino acid 3
  ( D ) OTHER INFORMATION: Xaa at position 3 is hydroxyproline ( x i ) SEQUENCE DESCRIPTION: SEQ ID NO:39:

Pro Ser Xaa Gly Asp Trp
            5

( 2 ) INFORMATION FOR SEQ ID NO:40:

( i ) SEQUENCE CHARACTERISTICS:
  ( A ) LENGTH: 6 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:40:

Pro Ser Pro Gly Asp Trp
            5

( 2 ) INFORMATION FOR SEQ ID NO:41:

( i ) SEQUENCE CHARACTERISTICS:
  ( A ) LENGTH: 6 amino acids
  ( B ) TYPE: amino acid
  ( D ) TOPOLOGY: linear ( i i ) MOLECULE TYPE: peptide ( i x ) FEATURE:
  ( B ) LOCATION: amino acid 4
  ( D ) OTHER INFORMATION: Xaa at position 4 is sarcosine ( x i ) SEQUENCE DESCRIPTION: SEQ ID NO:41:

Pro Ser Pro Xaa Asp Trp
            5

( 2 ) INFORMATION FOR SEQ ID NO:42:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:42:

Pro Ser Pro Ala Asp Trp
                  5

( 2 ) INFORMATION FOR SEQ ID NO:43:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:43:

Pro Ser Ser Gly Asp Trp
                  5

( 2 ) INFORMATION FOR SEQ ID NO:44:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( B ) LOCATION: amino acid 4
        ( D ) OTHER INFORMATION: Xaa at position 4 is sarcosine ( x i ) SEQUENCE DESCRIPTION: SEQ ID NO:44:

Pro Ser Ser Xaa Asp Trp
                  5

( 2 ) INFORMATION FOR SEQ ID NO:45:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:45:

Pro Ser Thr Gly Asp Trp
                  5

( 2 ) INFORMATION FOR SEQ ID NO:46:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( B ) LOCATION: amino acid 4
        ( D ) OTHER INFORMATION: Xaa at position 4 is sarcosine ( x i ) SEQUENCE DESCRIPTION: SEQ ID NO:46:

Pro Ser Thr Xaa Asp Trp
         5

( 2 ) INFORMATION FOR SEQ ID NO:47:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( B ) LOCATION: amino acid 3
        ( D ) OTHER INFORMATION: Xaa at position 3 is hydroxyproline ( x i ) SEQUENCE DESCRIPTION: SEQ ID NO:47:

Pro Ser Xaa Gly Asp Trp
         5

( 2 ) INFORMATION FOR SEQ ID NO:48:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( B ) LOCATION: amino acid 3
        ( D ) OTHER INFORMATION: Xaa at position 3 is hydroxyproline
        ( B ) LOCATION: amino acid 4
        ( D ) OTHER INFORMATION: Xaa at position 4 is sarcosine ( x i ) SEQUENCE DESCRIPTION: SEQ ID NO:48:

Pro Ser Xaa Xaa Asp Trp
         5

( 2 ) INFORMATION FOR SEQ ID NO:49:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( B ) LOCATION: amino acid 3
        ( D ) OTHER INFORMATION: Xaa at position 3 is dehydroproline ( x i ) SEQUENCE DESCRIPTION: SEQ ID NO:49:

Pro Ser Xaa Gly Asp Trp
         5

( 2 ) INFORMATION FOR SEQ ID NO:50:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( B ) LOCATION: amino acid 3
        ( D ) OTHER INFORMATION: Xaa at position 3 is dehydroproline
        ( B ) LOCATION: amino acid 4
        ( D ) OTHER INFORMATION: Xaa at position 4 is sarcosine ( x i ) SEQUENCE DESCRIPTION: SEQ ID NO:50:

Pro Ser Xaa Xaa Asp Trp
                  5

(2) INFORMATION FOR SEQ ID NO:51:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (B) LOCATION: amino acid 3
        (D) OTHER INFORMATION: Xaa at position 3 is 4-methyl proline (xi) SEQUENCE DESCRIPTION: SEQ ID NO:51:

Pro Ser Xaa Gly Asp Trp
                  5

(2) INFORMATION FOR SEQ ID NO:52:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (B) LOCATION: amino acid 3
        (D) OTHER INFORMATION: Xaa at position 3 is 4-methyl proline
        (B) LOCATION: amino acid 4
        (D) OTHER INFORMATION: Xaa at position 4 is sarcosine (xi) SEQUENCE DESCRIPTION: SEQ ID NO:52:

Pro Ser Xaa Xaa Asp Trp
                  5

(2) INFORMATION FOR SEQ ID NO:53:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (B) LOCATION: amino acid 3
        (D) OTHER INFORMATION: Xaa at position 3 is 4-methoxy proline (xi) SEQUENCE DESCRIPTION: SEQ ID NO:53:

Pro Ser Xaa Gly Asp Trp
                  5

(2) INFORMATION FOR SEQ ID NO:54:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (B) LOCATION: amino acid 3
        (D) OTHER INFORMATION: Xaa at position 3 is 4-methoxy proline
        (B) LOCATION: amino acid 4
        (D) OTHER INFORMATION: Xaa at position 4 is sarcosine (xi) SEQUENCE DESCRIPTION: SEQ ID NO:54:

Pro Ser Xaa Xaa Asp Trp
        5

( 2 ) INFORMATION FOR SEQ ID NO:55:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( i x ) FEATURE:
      ( B ) LOCATION: amino acid 3
      ( D ) OTHER INFORMATION: Xaa at position 3 is thioproline ( x i ) SEQUENCE DESCRIPTION: SEQ ID NO:55:

Pro Ser Xaa Gly Asp Trp
        5

( 2 ) INFORMATION FOR SEQ ID NO:56:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( i x ) FEATURE:
      ( B ) LOCATION: amino acid 3
      ( D ) OTHER INFORMATION: Xaa at position 3 is dimethyl thioproli ( x i ) SEQUENCE DESCRIPTION: SEQ ID NO:56:

Pro Ser Xaa Gly Asp Trp
        5

( 2 ) INFORMATION FOR SEQ ID NO:57:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( i x ) FEATURE:
      ( B ) LOCATION: amino acid 3
      ( D ) OTHER INFORMATION: Xaa at position 3 is dimethyl proline ( x i ) SEQUENCE DESCRIPTION: SEQ ID NO:57:

Pro Ser Xaa Gly Asp Trp
        5

( 2 ) INFORMATION FOR SEQ ID NO:58:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( i x ) FEATURE:
      ( B ) LOCATION: amino acid 3
      ( D ) OTHER INFORMATION: Xaa at position 3 is azetidine-
          carboxylic acid ( x i ) SEQUENCE DESCRIPTION: SEQ ID NO:58:

Pro Ser Xaa Gly Asp Trp
        5

( 2 ) INFORMATION FOR SEQ ID NO:59:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( B ) LOCATION: amino acid 3
    ( D ) OTHER INFORMATION: Xaa at position 3 is benzyloxycabonyl
          protected hydoxyproline ( x i ) SEQUENCE DESCRIPTION: SEQ ID NO:59:

Pro Ser Xaa Gly Asp Trp
              5

( 2 ) INFORMATION FOR SEQ ID NO:60:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( B ) LOCATION: amino acid 3
    ( D ) OTHER INFORMATION: Xaa at position 3 is D-proline ( x i ) SEQUENCE DESCRIPTION: SEQ ID NO:60:

Pro Ser Xaa Gly Asp Trp
              5

( 2 ) INFORMATION FOR SEQ ID NO:61:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:61:

Pro Ser Lys Gly Asp Trp
              5

( 2 ) INFORMATION FOR SEQ ID NO:62:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( B ) LOCATION: amino acid 3
    ( D ) OTHER INFORMATION: Xaa at position 3 is norvaline ( x i ) SEQUENCE DESCRIPTION: SEQ ID NO:62:

Pro Ser Xaa Gly Asp Phe
              5

( 2 ) INFORMATION FOR SEQ ID NO:63:

( i ) SEQUENCE CHARACTERISTICS:
    ( A ) LENGTH: 6 amino acids
    ( B ) TYPE: amino acid
    ( D ) TOPOLOGY: linear (i i) MOLECULE TYPE: peptide (i x) FEATURE:
    (B) LOCATION: amino acid 3
    (D) OTHER INFORMATION: Xaa at position 3 is norvaline
    (B) LOCATION: amino acid 6
    (D) OTHER INFORMATION: Xaa at position 6 is homophenylalanine (x i) SEQUENCE DESCRIPTION: SEQ ID NO:63:

Pro Ser Xaa Gly Asp Xaa
                    5

(2) INFORMATION FOR SEQ ID NO:64:

(i) SEQUENCE CHARACTERISTICS:
        (A) LENGTH: 6 amino acids
        (B) TYPE: amino acid
        (D) TOPOLOGY: linear (i i) MOLECULE TYPE: peptide (i x) FEATURE:
        (B) LOCATION: amino acid 3
        (D) OTHER INFORMATION: Xaa at position 3 is norvaline
        (B) LOCATION: amino acid 6
        (D) OTHER INFORMATION: Xaa at position 6 is O-methyl tyrosine (x i) SEQUENCE DESCRIPTION: SEQ ID NO:64:

Pro Ser Xaa Gly Asp Xaa
                    5

(2) INFORMATION FOR SEQ ID NO:65:

(i) SEQUENCE CHARACTERISTICS:
        (A) LENGTH: 6 amino acids
        (B) TYPE: amino acid
        (D) TOPOLOGY: linear (i i) MOLECULE TYPE: peptide (i x) FEATURE:
        (B) LOCATION: amino acid 3
        (D) OTHER INFORMATION: Xaa at position 3 is norvaline
        (B) LOCATION: amino acid 6
        (D) OTHER INFORMATION: Xaa at position 6 is cyclohexyl alanine (x i) SEQUENCE DESCRIPTION: SEQ ID NO:65:

Pro Ser Xaa Gly Asp Xaa
                    5

(2) INFORMATION FOR SEQ ID NO:66:

(i) SEQUENCE CHARACTERISTICS:
        (A) LENGTH: 6 amino acids
        (B) TYPE: amino acid
        (D) TOPOLOGY: linear (i i) MOLECULE TYPE: peptide (i x) FEATURE:
        (B) LOCATION: amino acid 3
        (D) OTHER INFORMATION: Xaa at position 3 is ornithine (x i) SEQUENCE DESCRIPTION: SEQ ID NO:66:

Pro Ser Xaa Gly Asp Trp
                    5

(2) INFORMATION FOR SEQ ID NO:67:

(i) SEQUENCE CHARACTERISTICS:
        (A) LENGTH: 4 amino acids (B) TYPE: amino acid
(D) TOPOLOGY: linear (ii) MOLECULE TYPE: peptide (xi) SEQUENCE DESCRIPTION: SEQ ID NO:67:

Arg Gly Asp Ser (2) INFORMATION FOR SEQ ID NO:68:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:68:

Arg Gly Asp Phe (2) INFORMATION FOR SEQ ID NO:69:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:69:

Gly Arg Gly Asp Ser Pro
                    5

(2) INFORMATION FOR SEQ ID NO:70:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:70:

Arg Gly Asp Ser (2) INFORMATION FOR SEQ ID NO:71:

(i) SEQUENCE CHARACTERISTICS:
(A) LENGTH: 6 amino acids
(B) TYPE: amino acid
(D) TOPOLOGY: linear (ii) MOLECULE TYPE: peptide (ix) FEATURE:
(B) LOCATION: amino acid 3
(D) OTHER INFORMATION: Xaa at position 3 is any amino acid
    other than an amino acid having a guanidino group at the
    side chain
(B) LOCATION: amino acid 4
(D) OTHER INFORMATION: Xaa at position 4 is any amino acid
(B) LOCATION: amino acid 6
(D) OTHER INFORMATION: Xaa at position 6 is an amino acid
    having a hydrophobic group at a side chain (xi) SEQUENCE DESCRIPTION: SEQ ID NO:71:

Pro Ser Xaa Xaa Asp Xaa
            5